(12) United States Patent
Rajan et al.

(10) Patent No.: US 10,562,931 B2
(45) Date of Patent: Feb. 18, 2020

(54) PROCESS FOR THE PREPARATION OF (1S, 4S, 7Z, 10S, 16E, 21R)-7-ETHYLDENE-4,21-BIS(1-METHYL-ETHYL)-2-OXA-12,13-DITHIA-5,8,20,23-TETRAAZABICYCLO[8.7.6]TRICOS-16-ENE-3, 6, 9, 19, 22-PENTONE

(71) Applicants: Srinivasan Thirumalai Rajan, Telangana (IN); Sajja Eswaraiah, Telangana (IN); Venkat Reddy Ghojala, Telangana (IN); MSN LABORATORIES PRIVATE LIMITED, Hyderabad, Telangana (IN)

(72) Inventors: Srinivasan Thirumalai Rajan, Telangana (IN); Sajja Eswaraiah, Telangana (IN); Venkat Reddy Ghojala, Telangana (IN)

(73) Assignee: MSN LABORATORIES PRIVATE LIMITED, Hyderabad, Telangana (IN)

( * ) Notice: Subject to any disclaimer, the term of this patent is extended or adjusted under 35 U.S.C. 154(b) by 0 days.

(21) Appl. No.: 15/770,118

(22) PCT Filed: Oct. 20, 2016

(86) PCT No.: PCT/IN2016/000255
§ 371 (c)(1),
(2) Date: Apr. 20, 2018

(87) PCT Pub. No.: WO2017/068596
PCT Pub. Date: Apr. 27, 2017

(65) Prior Publication Data
US 2018/0312538 A1    Nov. 1, 2018

(30) Foreign Application Priority Data
Oct. 20, 2015  (IN) .......................... 5640/CHE/2015

(51) Int. Cl.
*A61K 38/00*  (2006.01)
*C07K 5/103*  (2006.01)
*C07K 11/02*  (2006.01)
*C07K 1/02*   (2006.01)

(52) U.S. Cl.
CPC ............... *C07K 5/101* (2013.01); *C07K 1/02* (2013.01); *C07K 11/02* (2013.01)

(58) Field of Classification Search
None
See application file for complete search history.

(56) References Cited

PUBLICATIONS

Wen et al. J. Org. Chem. 2008, 73, 9353-9361.*

* cited by examiner

*Primary Examiner* — Jeanette M Lieb
(74) *Attorney, Agent, or Firm* — IP Pundit LLC

(57) ABSTRACT

The present invention is relates to an improved process for the preparation (1S,4S,7Z,10S,16E,21R)-7-ethylidene-4,21-bis(1-methylethyl)-2-oxa-12,13-dithia-5,8,20,23-tetraazabicyclo[8.7.6]tricos-16-ene-3,6,9,19,22-pentone of formula I.

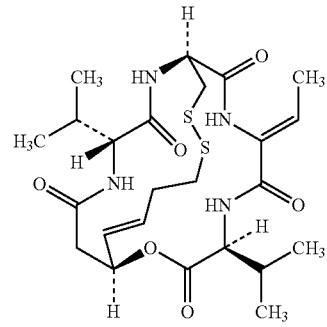

Formula-I

14 Claims, 2 Drawing Sheets

Figure 1:
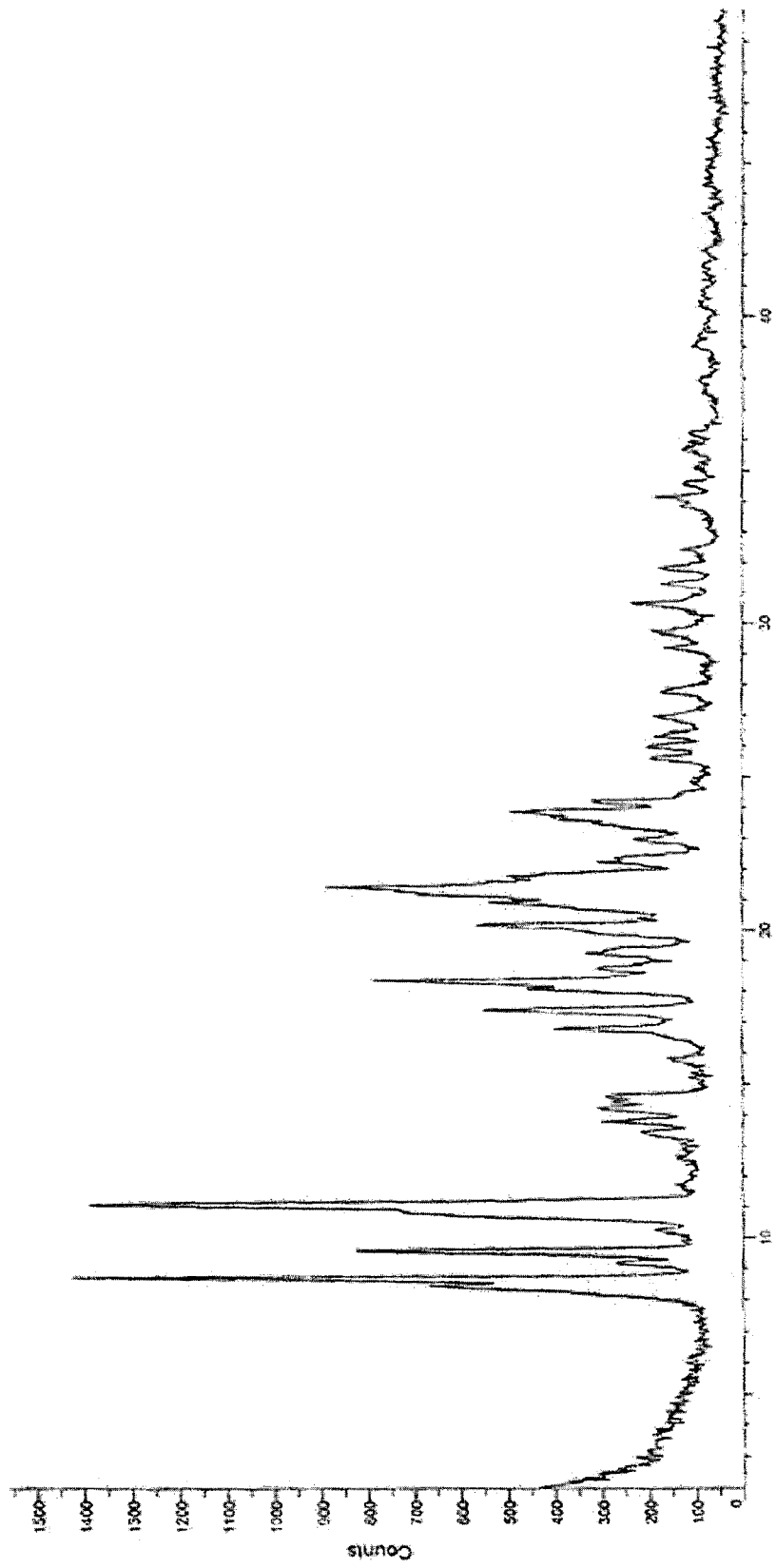

PROCESS FOR THE PREPARATION OF (1S, 4S, 7Z, 10S, 16E, 21R)-7-ETHYLDENE-4,21-BIS(1-METHYL-ETHYL)-2-OXA-12,13-DITHIA-5,8,20,23-TETRAAZABICYCLO[8.7.6]TRICOS-16-ENE-3, 6, 9, 19, 22-PENTONE

RELATED APPLICATION

This patent application is a national phase application under 35 U.S.C. § 371 of International Application No. PCT/IN2016/000255 filed on Oct. 20, 2016, which claims priority to Indian patent application number 5640/CHE/2015 filed on Oct. 20, 2015; the disclosure of which is incorporated herein by reference in its entirety.

FIELD OF THE INVENTION

The present invention is pertains to an improved process for the preparation of (1S,4S,7Z,10S,16E,21R)-7-ethylidene-4,21-bis(1-methylethyl)-2-oxa-12,13-dithia-5,8,20,23-tetraazabicyclo[8.7.6]tricos-16-ene-3,6,9,19,22-pentone, which is represented by the following formula I

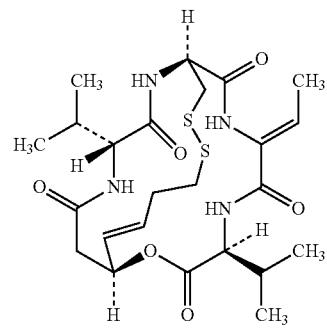

Formula-I

BACKGROUND OF THE INVENTION (1S,4S,7Z,10S,16E,21R)-7-ethylidene-4,21-bis(1-methylethyl)-2-oxa-12,13-dithia-5,8,20,23-tetraazabicyclo[8.7.6] tricos-16-ene-3,6,9,19,22-pentone of formula I is commonly known as "Romidepsin".

Romidepsin is a natural product and it is belongs to a class of histone deacetylase (HDAC) inhibitor, bicyclic depsipeptide. Romidepsin is approved for the treatment of cutaneous T-cell lymphoma (CTCL) and peripheral T-cell lymphoma (PTCL) in patients who have received at least one prior systemic therapy and it is marketed under the brand name of Istodax®.

U.S. Pat. No. 4,977,138 assigned to Fujisawa first disclosed the Romidepsin which is produced by fermantation of *Chromobacterium vilolaceum*.

*Journal of Organic Chemistry* 2008, 73, 9353-9361 reported a process for the preparation of Romidepsin as shown below:

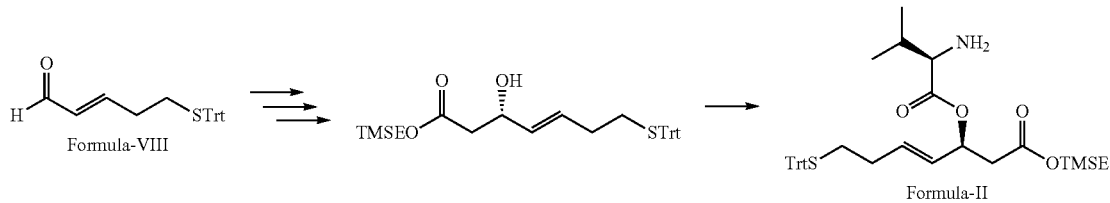

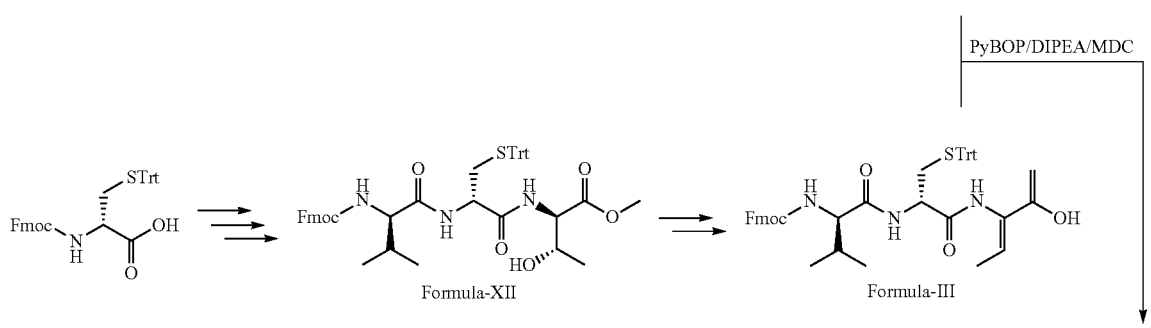

Romidepsin (I) ← 
1. Piperidine
2. TBAF, THF
3. HATU, DIPEA
4. I₂/MeOH

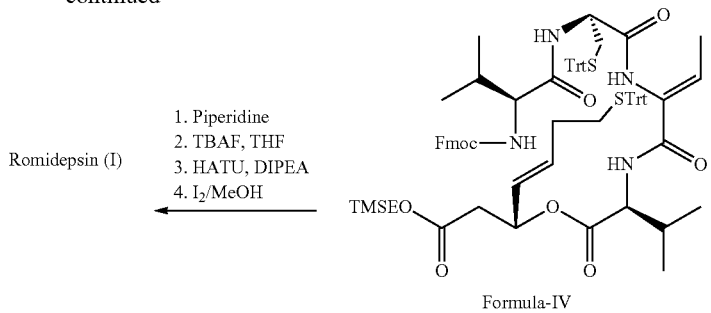

Formula-IV (E)-5-(Tritylthio)pent-2-enal of formula (VIII) and (6R, 9S,12S,13R) methyl 13-hydroxy-6-isopropyl-2,2-dimethyl-4,7,10-trioxo-9-(triphenylmethyl thiomethyl)-3-oxa-5,8,11-triazatetradecane-12-carboxylate of formula (XII) are key materials used in the preparation of intermediates of formulae II and III which are further coupling to produce Romidepsin.

The main drawback of the above process is the use of benzotriazol-1-yl-oxytripyrrolidinophosphonium hexafluorophosphate (PyBOP) as a coupling agent. PyBOP coupling agent is very difficult to handle and its contamination remains in the reaction mixture as it is not easily washable. Its removal from the product requires repeated column purifications which is commercially not viable.

Moreover, low temperatures are preferred for the condensation reactions (if the starting materials are chiral) which can control the racemization during the reaction. Using PyBOP and its analogue reagent (benzotriazol-1-yloxy)tris (dimethylamino)phosphonium hexafluorophosphate (BOP) requires high temperatures for carrying out reaction. Hence the use of condensation agents like BOP and PyBOP are not preferred for the coupling of chiral intermediates which lead to formation of racemic impurities and poor yield of the desired product.

*Journal of American Chemical Society* 1996, 7237-7238 reported a process for the preparation of Romidepsin comprising reacting the methyl pentadienoate with tritylthiol (also known as tritylthiol) in the presence Cs₂CO₃ followed by purification from flash chromatography to produce (2E)-5-tritylthio-2-pentenoic acid methyl ester, which is further reducing with diisobutyl aluminium hydride (DIBAL) and purified by flash chromatography to produce (2E)-5-tritylthio-2-pentenol. This (2E)-5-tritylthio-2-pentenol is oxidizing with oxalyl chloride in presence of dimethylsulfoxide (DMSO) followed by purification from flash chromatography to produce (E)-5-(tritylthio)pent-2-enal. This (E)-5-(tritylthio)pent-2-enal is reacted with O-benzyl, O-TMS ketene in presence of Ti(IV) catalyst to produce the aldol product which is hydrolyzed followed by condensation with D-valyl-D-cysteinyl-(S-trityl)-(Z)-dehydrobutinyl-L-valine, methyl ester to yield bis S-trityl ester product. This bis S-trityl ester product is hydrolyzed and reacted with DIAD in presence of PPh₃ and TsOH.H₂O to produce bis-(S-trityl) lactone which is further reacted with iodine in MeOH to produce Romidepsin.

The major drawback with the above prior art process is the use of BOP as a coupling agent which generates carcinogenic by-product hexamethylphosphoramide (HMPA). Therefore the handling of the BOP and the absence study for its by-product is highly critical. It is not suitable for a large scale process, therefore there is a need to develop an alternate process by avoiding the use of condensing agents like BOP.

Another disadvantage of the above process is the formation of unwanted β,γ isomer i.e. (3E)-5-tritylthio-3-pentenoic acid methyl ester as shown below

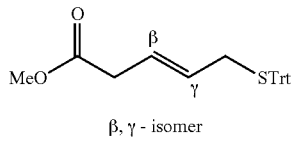

β, γ - isomer

Repeated purifications are required to remove this β,γ-isomer impurity which is very time consuming process and results decrease in the purity of final product.

Another disadvantage of the above process is oxidation involves the usage of oxalyl chloride in presence of DMSO and triethylamine in DCM solvent at −78° C. under nitrogen atmosphere. Handling of this reaction at very low temperature is highly critical and the by-product (dimethyl sulfide gas) evolved in this reaction which is unbearable and highly pungent smell.

*Organic Biomolecular Chemistry* 2011, 9, 3825-3833 reported a process for the preparation of (E)-5-(tritylthio) pent-2-enal of formula (VIII) comprising reaction of acrolein with tritylthiol to produce 3-tritylthiopropanal of formula (IX) which is further reacting with monoethyl malonate to produce the mixture of ethyl (E)-5-(tritylthio) pent-2-enoate of formula (X) and ethyl (E)-5-(tritylthio) pent-3-enoate of formula (Xa) followed by reducing with DIBAL to get the mixture of (E)-5-(tritylthio)pent-2-enol of formula (XI) and (E)-5-(tritylthio)pent-3-enol of formula (XIa) and finally oxidizing with oxalyl chloride in presence of DMSO to produce (E)-5-(tritylthio)pent-2-enal of formula (VIII).

The process is schematically shown as follows:

Scheme-2

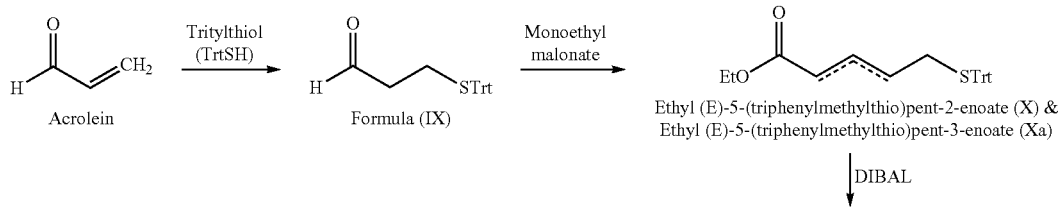

|DIBAL

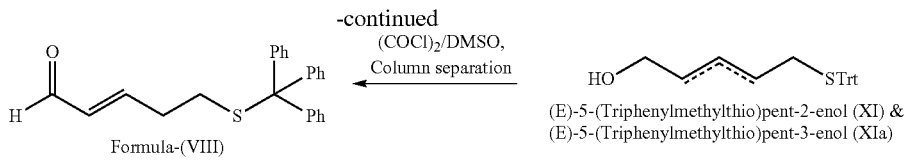

The major disadvantages with the above prior-art process are the formation of mixture of isomers such as ethyl (E)-5-(tritylthio)pent-3-enoate (X) and ethyl (E)-5-(tritylthio)pent-2-enoate (Xa); and (E)-5-(tritylthio)pent-3-enal (XI) & (E)-5-(tritylthio)pent-2-enal (XIa). Moreover, in this article, these isomers are separated by using column chromatography which is not suitable for industrial scale preparations.

Synlett 2012, 23(5), 783-787 reported a process for the preparation of (E)-5-(tritylthio)pent-2-enal of formula VIII comprising, reaction of acrolein with tritylthiol to give 3-(tritylthio)propanal of formula IX which is condensed with ethyl 2-(triphenylphosphoranylidene) acetate to produce (E)-ethyl 5-(tritylthio)pent-2-enoate of formula X followed by reducing with DIBAL-H and further oxidizing by Dess-Martine periodinane to produce (E)-5-(tritylthio)pent-2-enal of formula VIII.
The process is schematically shown as follows:

Removing TPPO impurity is very difficult as it is not soluble in most of organic solvents. TPPO impurity and unwanted isomer of formula Xb are soluble in alcohol solvents.

All the above prior art processes involves the use of column and flash chromatography methods to remove the TPPO and unwanted (Z)-5-(tritylthio)pent-2-enoate isomer of formula (Xb), which is tedious, laborious, requiring repeated purifications and also involving the use of large quantities of solvents. Hence it is not suitable at industrial scale operations.

Hence, there is a need to develop an improved process which is industrially feasible, eco-friendly, cost effective for the preparation of (E)-5-(tritylthio)pent-2-enal of formula X.

The present inventors had developed an improved process for the preparation of Romidepsin by avoiding all the aforementioned drawbacks in the prior art processes.

Scheme-3

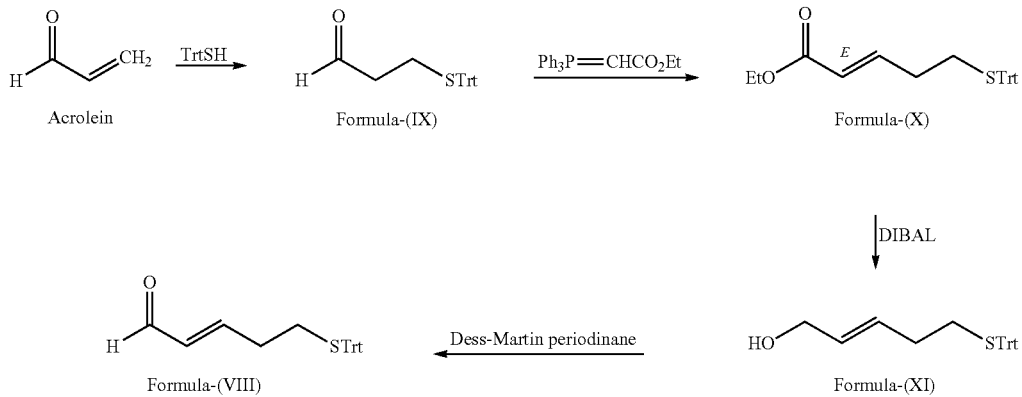

The major disadvantage with the above prior-art process is the formation of triphenylphosphine oxide (TPPO) and ethyl (Z)-5-(tritylthio)pent-2-enoate of formula (Xb) as an impurities.

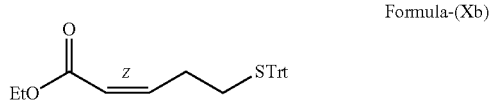

Formula-(Xb)

Impurity of formula (Xb) is generated along with required isomer ethyl (E)-5-(tritylthio)pent-2-enoate of formula (X).

This unwanted isomer or impurity of formula Xb is carried over in to the next stages and caused to the increase in impurities. Accordingly, the yield of required (E)-5-(tritylthio)pent-2-enal compound is reduced and also more purification steps are required to remove the impurities.

The present invention is also related to an improved process for the preparation of (E)-5-(tritylthio)pent-2-enal of formula (VIII) and (6R,9S,12S,13R) methyl 13-hydroxy-6-isopropyl-2,2-dimethyl-4,7,10-trioxo-9-(triphenylmethyl thiomethyl)-3-oxa-5,8,11-triazatetradecane-12-carboxylate of formula (XII) which are key components used in the preparation of vital intermediates of formulae (II) and (III) of Romidepsin.

Advantages of the Present Invention

Purification of (E)-5-(tritylthio)pent-2-enal of formula (VIII), 3-(tritylthio)propanal of formula (IX) involves isolation from suitable organic solvents to get good yield and good purity.
During the preparation of above intermediates (VIII) and (IX), triphenylphosphine oxide (TPPO) and (Z)-5-(tritylthio)pent-2-enoate impurity contamination found and these impurities are not easily removed with column purification methods. Whereas the present invention, purification of the same intermediates through isolation from organic solvents produces pure compounds.

Preparation of (6R,9S,12S,13R) methyl 13-hydroxy-6-isopropyl-2,2-dimethyl-4,7,10-trioxo-9-(triphenylmethyl thiomethyl)-3-oxa-5,8,11-triazatetradecane-12-carboxylate of formula (XII) involves dicyclohexylcarbodiimide (DCC) coupling agent is low cost material and it can be easily washable with water.

Preparation of (S,E)-3-hydroxy-7-(tritylthio)hept-4-enoic acid involves treating with di or tri carboxylic acid during work up which will reduces and washed out the titanium contamination One pot process for the preparation of (5R,8S,14S,Z)-(S,E)-1-oxo-1-(2-(trimethylsilyl)ethoxy)-7-(tritylthio) hept-4-en-3-yl 11-ethylidene-1-(9H-fluoren-9-yl)-5,14-diisopropyl-3,6,9,12-tetraoxo-8-((tritylthio)methyl)-2-oxa-4,7,10,13-tetraaza-pentadecan-15-oate of formula (IV)

One pot process for the preparation of (3S,9S,12R,16S,Z)-6-ethylidene-3,12-diisopropyl-16-((E)-4-(tritylthio)but-1-en-1-yl)-9-((tritylthio)methyl)-1-oxa-4,7,10,13-tetraazacyclohexadecane-2,5,8,11,14-pentaone of formula (VII).

BRIEF DESCRIPTION OF THE INVENTION

The first aspect of the present invention is to provide an improved process for the preparation of (1S,4S,7Z,10S,16E,21R)-7-ethylidene-4,21-bis(1-methylethyl)-2-oxa-12,13-dithia-5,8,20,23-tetraazabicyclo[8.7.6]tricos-16-ene-3,6,9,19,22-pentone (Romidepsin) of formula (I).

The second aspect of the present invention is to provide an improved process for the preparation of (E)-5-(tritylthio)pent-2-enal of formula (VIII).

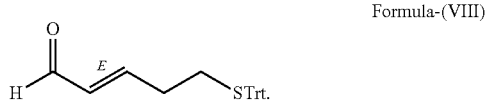
Formula-(VIII)

The third aspect of the present invention is to provide an improved process for the preparation of 3-(tritylthio)propanal of formula (IX)

Formula-(IX)

The fourth aspect of the present invention is to provide an improved process for the preparation of (6R,9S,12S,13R) methyl 13-hydroxy-6-isopropyl-2,2-dimethyl-4,7,10-trioxo-9-(triphenylmethyl thiomethyl)-3-oxa-5,8,11-triazatetradecane-12-carboxylate of formula (XII).

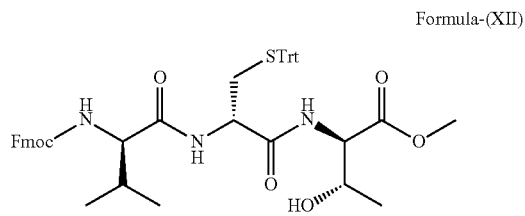
Formula-(XII)

The fifth aspect of the present invention is to provide an improved process for the preparation of (S,E)-3-hydroxy-7-(tritylthio)hept-4-enoic acid.

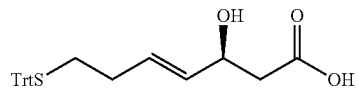

The sixth aspect of the present invention is to provide pure (5R,8S,14S,Z)-(S,E)-1-oxo-1-(2-(trimethylsilyl)ethoxy)-7-(tritylthio) hept-4-en-3-yl 11-ethylidene-1-(9H-fluoren-9-yl)-5,14-diisopropyl-3,6,9,12-tetraoxo-8-((tritylthio)methyl)-2-oxa-4,7,10,13-tetraazapenta decan-15-oate of formula (IV) having impurities less than 0.5% by HPLC in total of any combination of RSZSR impurity-1, RSZRS impurity-2 and RSZRR impurity-3.

The seventh aspect of the present invention is to provide one pot process for the preparation of (5R,8S,14S,Z)-(S,E)-1-oxo-1-(2-(trimethylsilyl)ethoxy)-7-(trityl thio)hept-4-en-3-yl 11-ethylidene-1-(9H-fluoren-9-yl)-5,14-diisopropyl-3,6,9,12-tetraoxo-8-((trityl thio) methyl)-2-oxa-4,7,10,13-tetraazapentadecan-15-oate of formula (IV).

The eight aspect of the invention is to provide one pot process for the preparation of (5R,8S,14S,Z)-(S,E)-1-oxo-1-(2-(trimethylsilyl)ethoxy)-7-(trityl thio) hept-4-en-3-yl 11-ethylidene-1-(9H-fluoren-9-yl)-5,14-diisopropyl-3,6,9,12-tetraoxo-8-((tritylthio)methyl)-2-oxa-4,7,10,13-tetraazapentadecan-15-oate of formula (VII).

The ninth aspect of the present invention is to provide crystalline form of Romidepsin and process for its preparation thereof.

BRIEF DISCUSSION OF THE DRAWINGS

FIG. 1: Illustrates the Powdered X-Ray Diffraction (PXRD) Pattern of the crystalline Form-M of Romidepsin FIG. 2: Illustrates the Powdered X-Ray Diffraction (PXRD) Pattern of the semi crystalline of Romidepsin

DETAILED DESCRIPTION OF THE INVENTION

The term "suitable solvent" used in the present invention refers to "hydrocarbon solvents" such as n-hexane, n-heptane, cyclohexane, pet ether, benzene, toluene, pentane, cycloheptane, methylcyclohexane, ethylbenzene, m-, o-, or p-xylene, octane, indane, nonane, or naphthalene and the like; "ether solvents" such as dimethoxymethane, tetrahydrofuran, 1,3-dioxane, 1,4-dioxane, furan, diethyl ether, ethylene glycol dimethyl ether, ethylene glycol diethyl ether, diethylene glycol dimethyl ether, diethylene glycol diethyl ether, triethylene glycol dimethyl ether, anisole, t-butyl methyl ether, 1,2-dimethoxy ethane and the like; "ester solvents" such as methyl acetate, ethyl acetate, isopropyl acetate, n-butyl acetate and the like; "polar-aprotic solvents such as dimethyl acetamide (DMA), dimethylformamide (DMF), dimethylsulfoxide (DMSO), N-methylpyrrolidone (NMP) and the like; "chloro solvents" such as dichloromethane, dichloroethane, chloroform, carbon tetrachloride and the like; "ketone solvents" such as acetone, methyl ethyl ketone, methyl isobutylketone and the like; "nitrile solvents" such as acetonitrile, propionitrile, isobutyronitrile and the like; "alcoholic solvents" such as methanol, ethanol, n-propanol, isopropanol, n-butanol, isobutanol, t-butanol, 2-nitroethanol, 2-fluoroethanol, 2,2,2-trifluoroethanol, ethylene glycol, 2-methoxyethanol, 1,2-ethoxyethanol, diethylene glycol, 1, 2, or 3-pentanol, neo-pentyl alcohol, t-pentyl alcohol, diethylene glycol monoethyl ether, cyclohexanol, benzyl alcohol, phenol, or glycerol and the like; "polar solvents" such as water or mixtures thereof.

The term "suitable base" used herein the present invention until unless specified is selected from inorganic bases like "alkali metal hydroxides" such as lithium hydroxide, sodium hydroxide, potassium hydroxide and the like; "alkali metal carbonates" such as sodium carbonate, potassium carbonate, lithium carbonate and the like; "alkali metal bicarbonates" such as sodium bicarbonate, potassium bicarbonate, lithium bicarbonate and the like; "alkali metal hydrides" such as sodium hydride, potassium hydride, lithium hydride and the like; "alkali metal alkoxides" such as sodium methoxide, sodium ethoxide, sodium tert-butoxide, potassium methoxide, potassium ethoxide, potassium tert-butoxide and the like; ammonia; and organic bases such as triethyl amine, diethylamine, trimethylamine, methyl amine, ethyl amine, tripropylamine, 1,8-diazabicyclo[5.4.0]undec-7-ene (DBU), 1,5-diazabicyclo(4.3.0)non-5-ene (DBN), lithium dioisopropylamide (LDA), n-butyl lithium, tribenzylamine, isopropyl amine, diisopropylamine (DIPA), diisopropylethylamine (DIPEA), N-methylmorpholine (NMP), N-ethylmorpholine, piperidine, dimethylaminopyridine (DMAP), morpholine, pyridine, 2,6-lutidine, 2,4,6-collidine, imidazole, I-methyl-imidazole, 1,2,4-triazole, 1,4-diazabicyclo[2.2.2]octane (DABCO) or mixtures thereof.

The term "suitable condensing agent" used herein the present invention until unless specified is selected from N,N-carbonyldiimidazole (CDI); alkyl and aryl carbodiimides such as N,N-diisopropylcarbodiimide (DIC), N,N-dicyclohexyl carbodiimide (DCC), 1-ethyl-3-(3-dimethylaminopropyl)carbodiimide hydrochloride (EDC.HCl), (1-[bis (dimethylamino) methylene]-1H-1,2,3-triazolo[4,5-b] pyridinium3-oxidhexafluoro phosphate (HATU), hydroxy benzotriazole (HOBt), 1-hydroxy-2,5-pyrrolidinedione (HOSu), ditolyl carbodiimide optionally in combination with hydroxybenzotriazole or N-hydroxysuccinimide (NHS) or N-hydroxysulfosuccinimide (Sulfo-NHS); carbonyl-di-1,2,4-triazole.

The first aspect of the present invention provides an improved process for the preparation of (1S,4S,7Z,10S,16E, 21R)-7-ethylidene-4,21-bis(1-methylethyl)-2-oxa-12,13-dithia-5,8,20,23-tetraazabicyclo[8.7.6]tricos-16-ene-3,6,9, 19,22-pentone of formula (I), comprising the steps of:
 a) condensing (S,E)-2-(trimethylsilyl)ethyl 3-(((S)-2-amino-3-methylbutanoyl) oxy)-7-(tritylthio)hept-4-enoate of formula (II) with (5R,8S,Z)-1-(9H-fluoren-9-yl)-5-isopropyl-3,6,9-trioxo-8-(tritylthiomethyl)-2-oxa-4,7,10-triazatridec-11-ene-11-carboxylic acid of formula (III) in presence of a condensing agent and an organic base in a organic solvent to provide (5R,8S, 14S,Z)-(S,E)-1-oxo-1-(2-(trimethylsilyl)ethoxy)-7-(tritylthio)hept-4-en-3-yl 11-ethylidene-1-(9H-fluoren-9-yl)-5,14-diisopropyl-3,6,9,12-tetraoxo-8-((tritylthio) methyl)-2-oxa-4,7,10,13-tetraaza-pentadecan-15-oate of formula (IV),

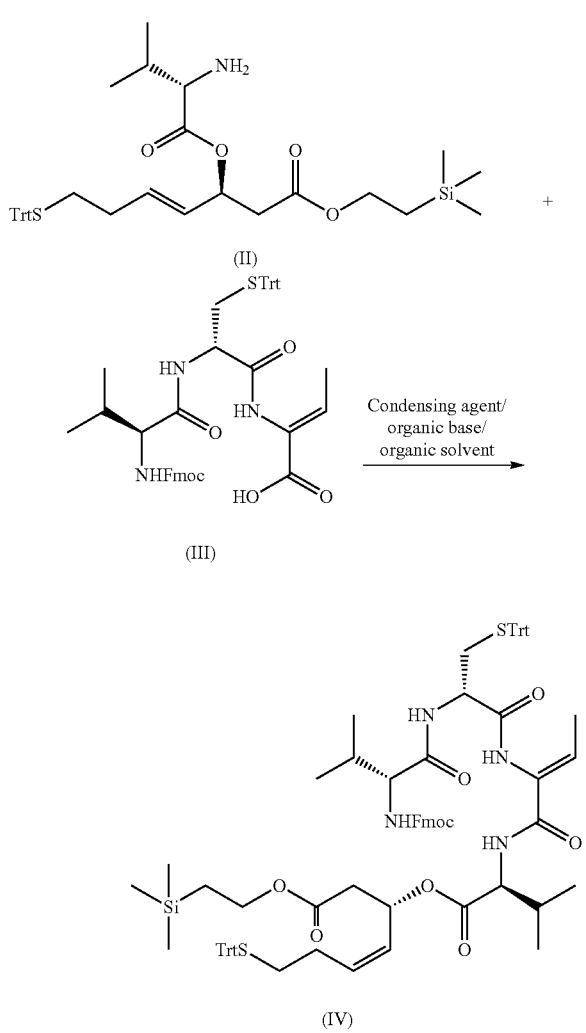

wherein, the condensing agent is selected from (1-[bis (dimethylamino) methylene]-1H-1,2,3-triazolo[4,5-b]pyridinium3-oxidhexafluoro phosphate (HATU), hydroxy benzotriazole (HOBt), dicyclohexylcarbodiimide (DCC), 1-hydroxy-2,5-pyrrolidinedione (HOSu); the organic base is selected from diisopropylethylamine (DIPEA), triethylamine (TEA), N-methylmorpholine (NMM) or mixtures thereof; the organic solvent is selected from dichloromethane, chloroform, acetonitrile, tetrahydrofuran, ethyl acetate or mixtures thereof, b) deprotecting the compound of formula (IV) with alkylamine in presence of a polar aprotic solvent to get (S,E)-2-(trimethylsilyl)ethyl 3-(((S)-2-((Z)-2-((S)-2-((R)-2-amino-3-methylbutanamido)-3-(tritylthio)propanamido)but-2-enamido)-3-methyl butanoyl)oxy)-7-(tritylthio)hept-4-enoate of formula (V)

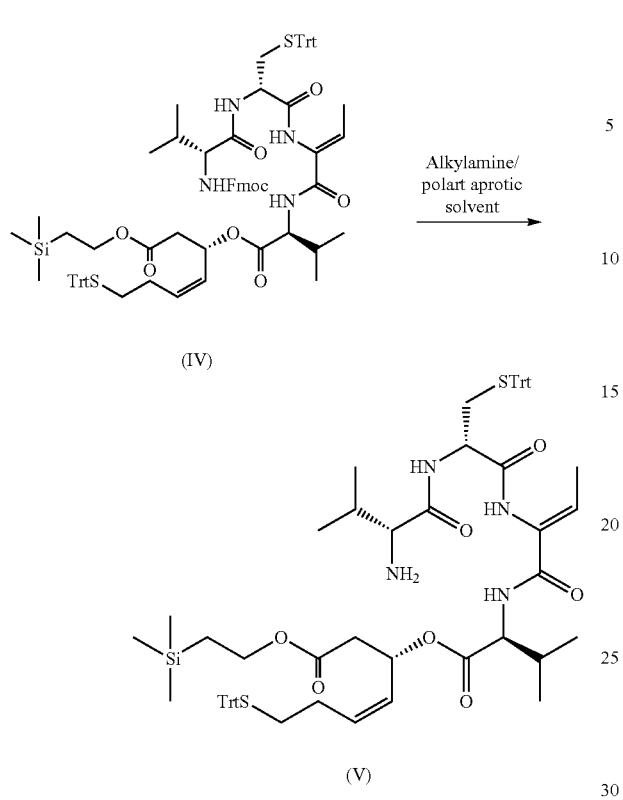

(IV)

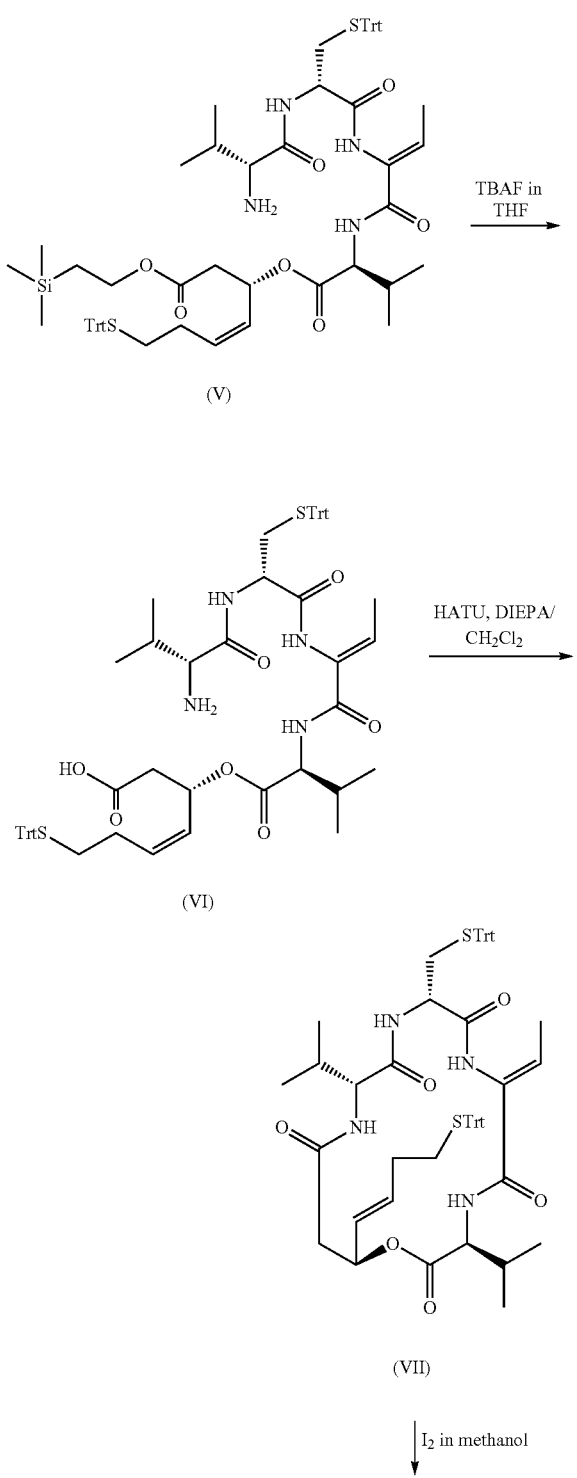

wherein, the alkylamine is selected from diethylamine, dimethylamine, triethylamine, diisopropylethylamine, tripropylamine, n-butylamine or mixtures thereof; and polar aprotic solvent is selected from acetonitrile, dimethyl sulfoxide, dimethylacetamide, dimethylformamide, tetrahydrofuran, N-methylpyrrolidinone, c) converting the compound of formula (V) to the compound of formula (I).

In the present aspect of the invention, the coupling of compound of formula (II) with the compound of formula (III) is carried out by using HATU and HOBt at 0-5° C. in dichloromethane in presence of DIPEA to get the compound of formula (IV).

The main advantage of the present invention is coupling of chiral intermediate compounds of formulae (II) and (III) in presence of carbodiimide coupling agents at low temperatures controls the racemization.

Deprotection of Fmoc protecting group from compound of formula (IV) using cyclic organic base such as piperidine (prior-art process) results the formation of higher level of impurities, whereas the present invention involves the usage of alkylamine base preferably diethylamine, reduces the formation of impurities or side products and thereby providing the desired compound high purity.

The compound of formula V can be converted to the compound of formula I by known methods in the art as follows:

a. the compound of formula (V) is treated with TBAF in THF to produce (3S,6S,12S,15R,Z)-15-amino-9-ethylidene-6-isopropyl-16-methyl-5,8,11,14-tetra oxo-3-((E)-4-(tritylthio)but-1-en-1-yl)-12-((triphenylmethylthio)methyl)-4-oxa-7,10,13-triazaheptadecan-1-oic acid of formula (VI), b. the compound of formula VI is internally condensed in presence of HATU, DIPEA in dichloromethane to produce (3S,9S,12R,16S,Z)-6-ethylidene-3,12-diisopropyl-16-((E)-4-(tritylthio)but-1-en-1-yl)-9-((tritylthio)methyl)-1-oxa-4,7,10,13-tetraaza cyclohexadecane-2,5,8,11,14-pentaone of formula (VII), c. the compound of formula (VII) is reacted with iodine in methanol to produce the compound of formula (I).

-continued

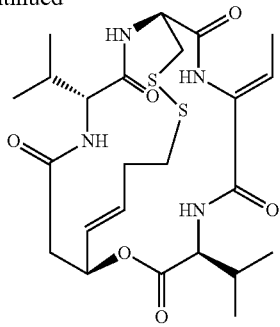

Romidepsin (I)

The another aspect of the present invention provides a process for the preparation of compound of formula I comprising:
  a. treating the compound of formula (IV) with tetrabutylammonium fluoride (TBAF) in an organic solvent to provide the compound of formula (VI);
  b. converting the compound of formula VI to the compound of formula I.

In step-a), (5R,8S,14S,Z)-(S,E)-1-oxo-1-(2-(trimethylsilyl)ethoxy)-7-(tritylthio)hept-4-en-3-yl 11-ethylidene-1-(9H-fluoren-9-yl)-5,14-diisopropyl-3,6,9,12-tetraoxo-8-((tritylthio) methyl)-2-oxa-4,7,10,13-tetraaza-pentadecan-15-oate of formula (IV) (NH-Fmoc and COO—Si diprotected compound) in organic solvent is treated with tetrabutylammonium fluoride (TBAF) in a polar aprotic solvent at 0-5° C. provides amino acid compound of formula (VI).

The second aspect of the present invention provides an improved process for the preparation of (E)-5-(tritylthio)pent-2-enal compound of formula (VIII), comprising of:
  a) reacting 3-(tritylthio)propanal of formula (IX) with ethyl 2-(triphenyl phosphoranylidene)acetate in an organic solvent, and
  b) purifying the compound obtained in step-a) from suitable organic solvent get pure (E)-ethyl 5-(tritylthio)pent-2-enoate of formula (X),

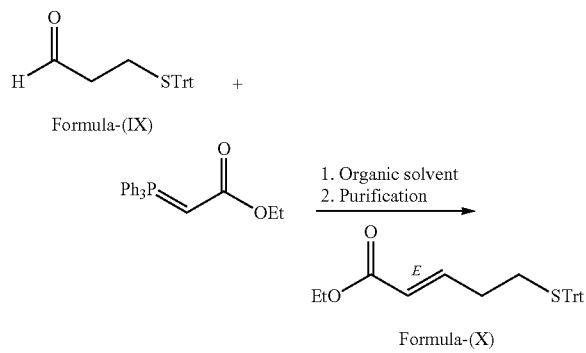

c) reducing pure (E)-ethyl 5-(tritylthio)pent-2-enoate of formula (X) using a suitable reducing agent, and
  d) purifying the compound obtained in step-c) from suitable organic solvent to get pure (E)-5-(tritylthio)pent-2-ene-1-ol of formula (XI),

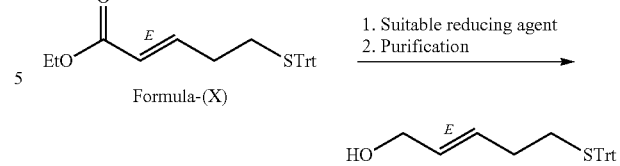

e) oxidizing pure (E)-5-(tritylthio)pent-2-ene-1-ol of formula (XI) using $MnO_2$ in presence of organic solvent, and
  f) purifying the compound obtained in step-e) from suitable organic solvent to get pure (E)-5-(tritylthio)pent-2-enal of formula (VIII),

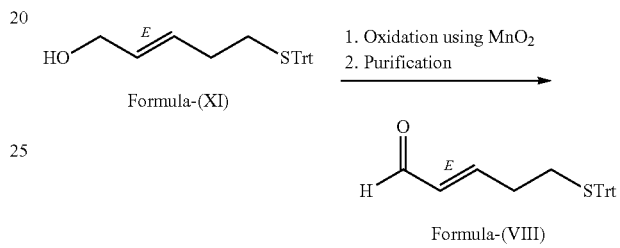

wherein, the purification in step-b), step-d) and step-f) is carried by the crystallization, recrystallization or distillation from suitable organic solvent selected from polar protic solvents, polar aprotic solvents and non polar solvents or mixtures thereof.

The polar protic solvent is selected from alcohols for example methanol, ethanol, n-propanol, iso-propanol, n-butanol, isobutanol, tertiary butanol, trifluoroethanol, methoxy ethanol, ethylene glycol; and water and the like.

The polar aprotic solvent is selected from esters such as methyl acetate, ethyl acetate, isopropyl acetate; ketones such as acetone, butanone, pentanone; nitriles such as acetonitrile, propionitrile; dimethyl formamide (DMF), dimethyl sulfoxide (DMSO), tetrahydrofuran (THF), dimethyl acetamide (DMAc), N-methyl morpholine (NMP) and the like.

The non polar solvent is selected from hexane, heptane, cyclohexane, toluene, trifluorotoluene, chlorobenzene, tert-butyl-methyl ether, cyclopentylmethyl ether, dichloromethane and the like.

The suitable reducing agent is selected from DIBAL-H, sodium borohydride, lithium aluminum hydride and the like, more preferably DIBAL-H.

The step-a), step-b) and step-c) are carried out in presence of a organic solvent which is selected from halo hydrocarbons such as chloromethane, dichloromethane, chloroform, carbon tetrachloride, ethylene dichloride, chlorobenzene; esters such as ethyl acetate, methyl acetate, propyl acetate, isopropyl acetate; nitrile solvents such as acetonitrile, propionitrile; DMF, DMAc, THF, methyl tertiary butyl ether, N-methyl pyrrolidinone, DMSO.

The 3-(tritylthio)propanal of formula (IX) is reacted with ethyl 2-(triphenyl phosphoranylidene)acetate in dichloromethane at 30° C. and purified by isolation from methanol to provide pure (E)-ethyl 5-(tritylthio)pent-2-enoate of formula (X).

The pure compound of formula (X) is reduced by using DIBAL-H at room temperature to get the (E)-5-(tritylthio)

pent-2-ene-1-ol of formula (XI) which is purified by isolation from toluene to provide the pure compound (E)-5-(tritylthio)pent-2-ene-1-ol of formula (XI).

The pure compound of formula (XI) is oxidized by using MnO₂ in dichloromethane to get a compound of formula (VIII). The compound of formula (VIII) is purified by isolation from isopropanol.

The main advantage of the present invention is that, it greatly reduced the amount of impurities such as TPPO, β,γ-isomer of formula (Xa) and Z-isomer of formula (Xb) in required compound (E)-ethyl 5-(tritylthio)pent-2-enoate of formula (X) when purified by recrystallization from organic solvents, preferably from methanol and accordingly the use of flash and column chromatographic methods are avoided. This has a great impact during industrial scale-up.

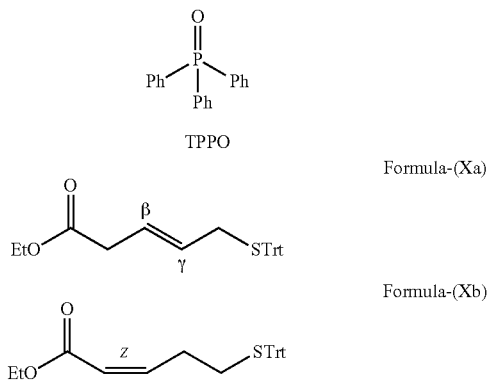

The compound of formula (VIII) can be converted to the compound of formula (II) by known methods in the prior arts.

The third aspect of the present invention provides an improved process for the preparation of 3-(tritylthio)propanal of formula (IX), comprising the steps of:

a) 3-(tritylthio)propionic acid of formula (XIX) is reduced by using a suitable reducing agent in an organic solvent to provide 3-(tritylthio)propan-1-ol of formula (XX);

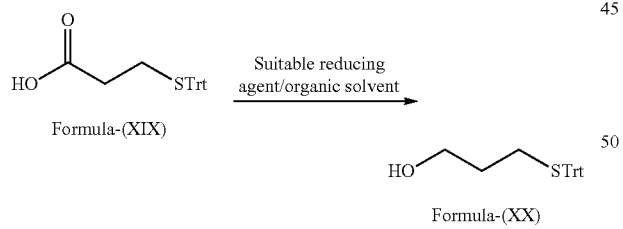

b) purifying the compound of formula (XX) obtained in step-a) from a suitable solvent to provide pure 3-(tritylthio)propan-1-ol of formula (XX);

c) oxidation of pure compound of formula (XX) using oxalyl chloride in presence of DMSO to provide 3-(tritylthio)propanal of formula (IX)

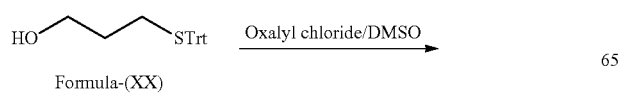

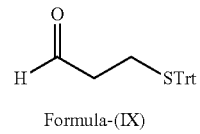

Formula-(IX)

wherein, the suitable solvent for the purification is selected from alkanes such as cyclohexane, cyclopentane, cyclobutane n-hexane etc. Preferably cyclohexane.

The suitable reducing agent is selected from sodium borohydride, boron trifluoride etherate, boron etherate, lithium aluminum hydride or mixtures thereof and the like. More preferably sodium borohydride and boron trifluoride etherate.

3-(Tritylthio) propionic acid of formula (XIX) in tetrahydrofuran is reduced by using sodium borohydride and boron trifluoride.etherate at 0-5° C. to get 3-(tritylthio)propan-1-ol of formula XX. This crude compound is purified by recrystallization from cyclohexane to get pure product. This pure product is oxidized by using oxalyl chloride in presence of DMSO at room temperature in presence of triethylamine to provide 3-(tritylthio)propanal of formula (IX).

The fourth aspect of the present invention provides an improved process for the preparation of (6R,9S,12S,13R) methyl 13-hydroxy-6-isopropyl-2,2-dimethyl-4,7,10-trioxo-9-(tritylthiomethyl)-3-oxa-5,8,11-triazatetradecane-12-carboxylate of formula (XII), comprising the steps of:

a) reacting (D)-tritylthio cysteine of formula (XIII) with fluorenylmethoxycarbonyl chloride (Fmoc-Cl) in presence of a base in polar aprotic solvent to provide fluorenylmethoxycarbonylamino (D)-tritylthio cysteine of formula (XIV)

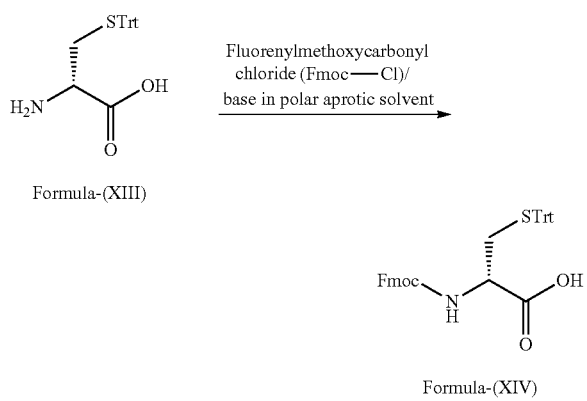

b) reacting the fluorenylmethoxycarbonylamino (D)-tritylthio cysteine of formula (XIV) with (2S,3R) methyl 2-amino-3-hydroxy butanoate hydrochloride of formula (XV) in presence of a condensing agent and base in organic solvent to produce methyl 2-((S)-2-(((9H-fluoren-9-yl)methoxy)carbonylamino)-3-(tritylthio) propanamido)-3-hydroxy butanoate of formula (XVI) which is further in-situ treatment with organic base in polar aprotic solvent to produce (2S,3R)-methyl 2-((S)-2-amino-3-(tritylthio)propanamido)-3-hydroxy butanoate of formula (XVII)

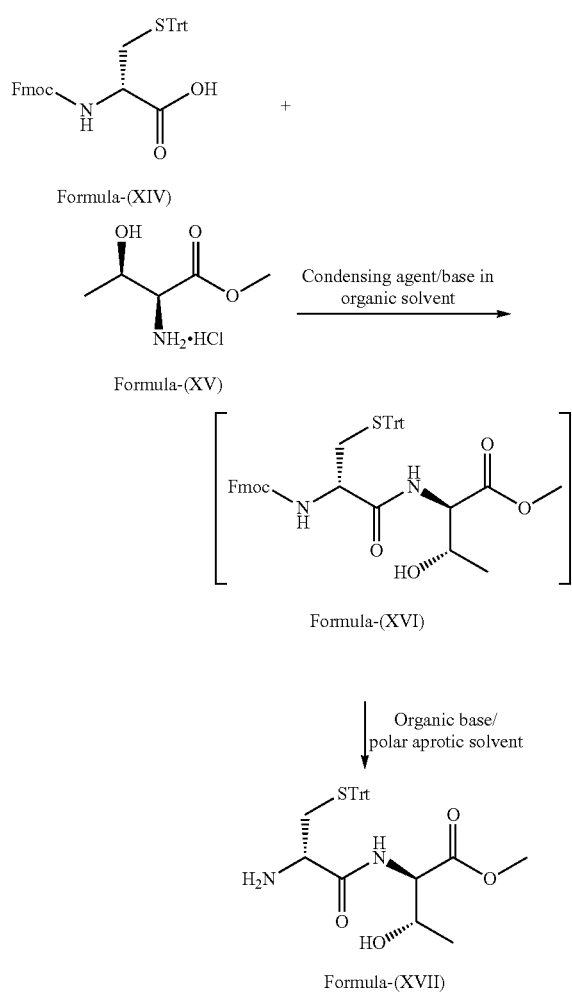

Formula-(XIV)

Formula-(XV)

Formula-(XVI)

Formula-(XVII)

wherein, the condensing agent is selected from the group comprising of DCC, HOBt, N-hydroxylsuccinimide (HOSu), 3-hydroxy-1,2,3-benzotriazin-4-[3H]-one; an organic base is selected from triethylamine, diethylamine, diisopropylethylamine, n-butylamine, pyridine.

c) Reacting the (2S,3R) Methyl 2-((S)-2-amino-3-(tritylthio)propanamido)-3-hydroxy butanoate of formula (XVII) with fluorenylmethoxycarbonylamino-D-valine of formula (XVIII) in presence of a condensing agent in an organic solvent to provide (6R,9S,12S,13R) methyl 13-hydroxy-6-isopropyl-2,2-dimethyl-4,7,10-trioxo-9-(tritylthiomethyl)-3-oxa-5,8,11-triazatetradecane-12-carboxylate of formula (XII)

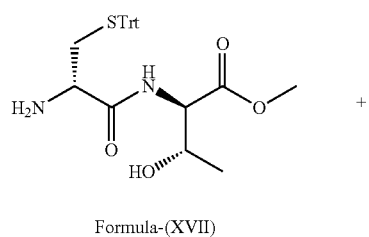

Formula-(XVII)

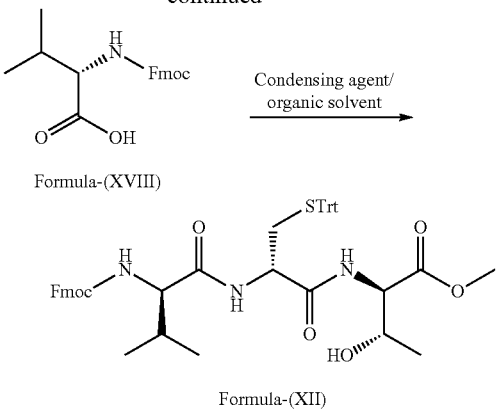

Formula-(XVIII)

Formula-(XII)

The preferred embodiment of the present invention provides a process for the preparation of compound of formula (XII) comprising of:
a) reacting the (D)-tritylthio cysteine of formula (XIII) with fluorenylmethoxycarbonyl chloride (Fmoc-Cl) in presence of sodium bicarbonate in tetrahydrofuran to provide fluorenylmethoxycarbonylamino (D)-tritylthio cysteine of formula (XIV),
b) reacting the compound of formula (XIV) with (2S,3R) methyl 2-amino-3-hydroxy butanoate hydrochloride of formula (XV) in presence of dicyclohexylcarbodiimide, hydroxybenzotriazole, N-methylmorpholine to get methyl 2-((S)-2-(((9H-fluoren-9-yl)methoxy)carbonylamino)-3-(tritylthio) propanamido)-3-hydroxy butanoate of formula (XVI) which on in-situ treatment with triethylamine in acetonitrile to provide (2S,3R)-methyl 2-((S)-2-amino-3-(tritylthio)propanamido)-3-hydroxy butanoate of formula (XVII),
c) reacting the compound of formula (XVII) with the compound of formula (XVIII) in presence of dicyclohexylcarbodiimide, hydroxybenzotriazole, N-methylmorpholine to provide (6R,9S,12S,13R) methyl 13-hydroxy-6-isopropyl-2,2-dimethyl-4,7,10-trioxo-9-(tritylthiomethyl)-3-oxa-5,8,11-triazatetradecane-12-carboxylate (XII).

The compound of formula (XII) can be converted to the compound of formula (III) by known methods in the prior art.

The fifth aspect of the present invention provides an improved process for the preparation of (S,E)-3-hydroxy-7-(tritylthio)hept-4-enoic acid, comprising:

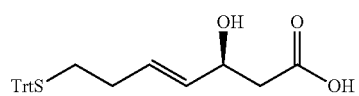

a) reacting (R)-4-isopropylthiazolidine-2-thione with acetyl chloride in presence of a suitable base and suitable organic solvent,
b) coupling the product obtained in step-a) with (E)-5-(tritylthio)pent-2-enal in presence of titanium tetrachloride and a suitable base and suitable organic solvent,
c) adding suitable carboxylic acid to the reaction mixture,
d) hydrolyzing the reaction mixture with aqueous alkaline solution to get (S,E)-3-hydroxy-7-(tritylthio)hept-4-enoic acid.

wherein,
the suitable base and suitable organic solvent used in step-a) and step-b) of the above process is selected from pyridine, pyrrole and alkylamine such as methylamine, dimethylamine, ethylamine, diethylamine, triethylamine, diisopropylethylamine (DIPEA) and the like; halohydrocarbon solvents such as dichloromethane, trichloromethane, tetrachloromethane (chloroform), chlorobenzene; ester solvents such as methyl acetate, ethyl acetate, isopropyl acetate; ether solvents such as diethyl ether, diisopropyl ether and tetrahydrofuran (THF); nitrile solvents such as acetonitrile, propionitrile and the like.
the suitable carboxylic acid used in step-c) is selected from di or tri carboxylic acid such as aqueous tartaric acid, aqueous citric acid, fumaric acid, malic acid or the mixtures thereof. Preferably aqueous tartaric acid.
After completion of coupling reaction in step-b, the titanium contamination remained as in impurity in the resulting reaction mixture. The formed titanium impurity can be washed out as dihydroxytitanium (IV) chloride complex when washing the reaction mixture with suitable di or tri carboxylic acid.
Aqueous alkaline solution in step-d can be selected from aqueous hydroxide or carbonate or dicarbonate solutions of lithium, sodium or potassium.

The sixth aspect of the present invention provides (5R, 8S,14S,Z)-(S,E)-1-oxo-1-(2-(trimethylsilyl)ethoxy)-7-(tritylthio) hept-4-en-3-yl 11-ethylidene-1-(9H-fluoren-9-yl)-5, 14-diisopropyl-3,6,9,12-tetraoxo-8-((tritylthio) methyl)-2-oxa-4,7,10,13-tetraazapenta decan-15-oate of formula (IV) having impurities of RSZSR impurity-1, RSZRS impurity-2 and RSZRR impurity-3 less than 0.5% by chiral HPLC.

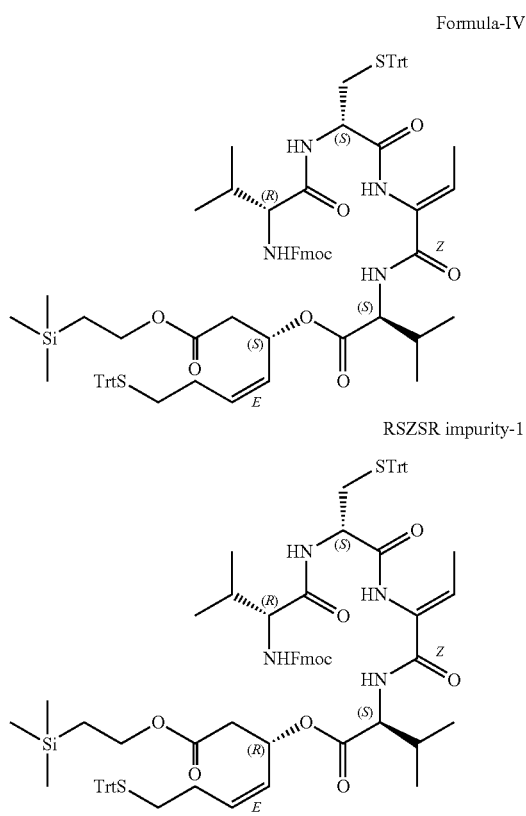

Formula-IV

RSZSR impurity-1

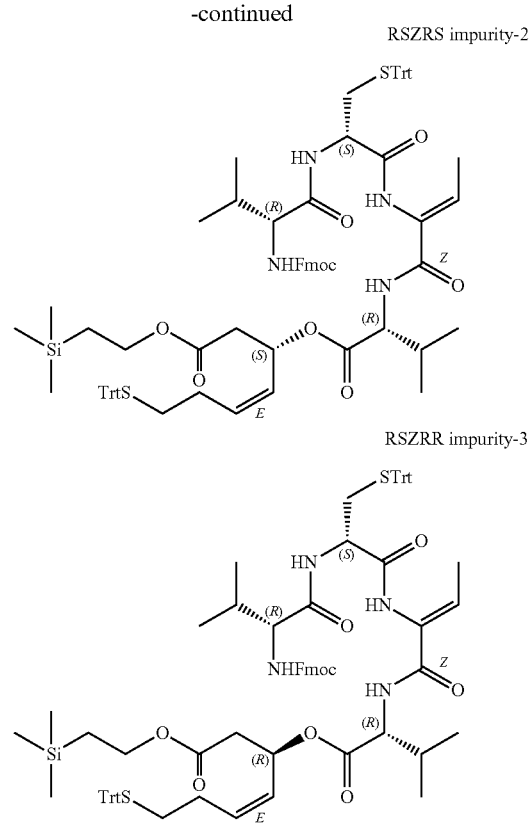

RSZRS impurity-2

RSZRR impurity-3

In another aspect of the present invention provides a process for the purification of crude (5R,8S,14S,Z)-(S,E)-1-oxo-1-(2-(trimethylsilyl)ethoxy)-7-(tritylthio) hept-4-en-3-yl 11-ethylidene-1-(9H-fluoren-9-yl)-5,14-diisopropyl-3, 6,9,12-tetraoxo-8-((tritylthio) methyl)-2-oxa-4,7,10,13-tetraazapenta decan-15-oate of formula (IV) comprising:
a) subjecting crude compound of formula (IV) to chromatography to form a product, wherein the chromatography is carried out using an achiral stationary phase comprising silica and an eluent comprising ethyl acetate and an apolar solvent, and wherein the apolar solvent is selected from heptane, and cyclohexane; and
b) distillating the product obtained in step (a) from a solvent selected from heptane, ethers, acetonitrile, alcohols, esters, or mixtures of any of these solvents to form pure compound of formula IV having impurities RSZSR impurity-1, RSZRS impurity-2 and RSZRR impurity-3 less than 0.5% by HPLC.

The seventh aspect of the present invention provides one pot process for the preparation of (5R,8S,14S,Z)-(S,E)-1-oxo-1-(2-(trimethylsilyl)ethoxy)-7-(trityl thio) hept-4-en-3-yl 11-ethylidene-1-(9H-fluoren-9-yl)-5,14-diisopropyl-3,6, 9,12-tetraoxo-8-((tritylthio) methyl)-2-oxa-4,7,10,13-tetraazapentadecan-15-oate of formula (IV), comprising: a) reacting (S,E)-3-hydroxy-7-(tritylthio)hept-4-enoic acid with 2-(trimethylsilyl)ethanol in presence of suitable coupling agent, suitable organic base in organic solvent,
b) reacting the product obtained in step-a with Fmoc-L-valine in presence of suitable coupling agent, suitable organic base in organic solvent,
c) deprotecting the product obtained in step-b with alkylamine in organic solvent,
d) reacting the product obtained in step-c with the compound of formula (III) in presence of suitable coupling agent, suitable organic base in organic solvent.

Wherein, in step-a and step-b) the suitable coupling agent selected from N,N-carbonyldiimidazole (CDI), alkyl and aryl carbodiimides such as N,N-diisopropylcarbodiimide (DIC), N,N-dicyclohexyl carbodiimide (DCC). Preferably DCC; the suitable organic base used in step-a and step-b selected from dimethylaminopyridine (DMAP), isopropyl amine, diisopropylamine (DIPA), diisopropylethylamine (DIPEA), N-methylmorpholine (NMP), N-ethylmorpholine, piperidine. Preferably dimethylaminopyridine (DMAP); the suitable organic solvent used in step-a and step-b is selected from "chloro solvents" such as dichloromethane, dichloroethane, chloroform, carbon tetrachloride and the like; "ketone solvents" such as acetone, methyl ethyl ketone, methyl isobutylketone and the like; "nitrile solvents" such as acetonitrile, propionitrile, isobutyronitrile and the like; "alcoholic solvents" such as methanol, ethanol, n-propanol, isopropanol, n-butanol, isobutanol. Preferably, dichloromethane.

In step-c) the alkylamine is selected from triethyl amine, diethylamine, trimethylamine, methyl amine, ethyl amine, tripropylamine; the organic solvent is acetonitrile, tetrahydrofuran, ethyl acetate. Preferably, acetonitrile.

In step-d) the coupling agent is selected from 1-ethyl-3-(3-dimethylaminopropyl)carbodiimide hydrochloride (EDC.HCl), (1-[bis(dimethylamino) methylene]-1H-1,2,3-triazolo[4,5-b]pyridinium3-oxidhexafluoro phosphate (HATU), hydroxy benzotriazole (HOBt), 1-hydroxy-2,5-pyrrolidinedione (HOSu), ditolyl carbodiimide optionally in combination with hydroxybenzotriazole or N-hydroxysuccinimide (NHS) or N-hydroxysulfosuccinimide (Sulfo-NHS) or mixtures thereof. Preferably EDC. HCl and HOBT mixture; the suitable organic solvent is acetonitrile, tetrahydrofuran, ethyl acetate. Preferably, acetonitrile.

The eighth aspect of the present invention provides one pot process for preparation of (5R,8S,14S,Z)-(S,E)-1-oxo-1-(2-(trimethylsilyl)ethoxy)-7-(trityl thio) hept-4-en-3-yl 11-ethylidene-1-(9H-fluoren-9-yl)-5,14-diisopropyl-3,6,9,12-tetraoxo-8-((tritylthio)methyl)-2-oxa-4,7,10,13-tetraazapentadecan-15-oate of formula (VII) comprising:
a) treating the compound of formula (IV) with suitable alkylamine in a suitable organic solvent,
b) deprotecting the product obtained in step-b with suitable deprotecting agent in a suitable solvent,
c) cyclizing the product obtained in step-c in presence of suitable coupling agent in presence of suitable organic base in organic solvent.

Wherein, in step-a) the suitable alkylamine is selected from triethyl amine, diethylamine, trimethylamine, methyl amine, ethyl amine, tripropylamine. Preferably diethylamine. The organic solvent is selected from nitrile solvents, ester solvents, ketone solvents, ether solvents and the like. Preferably nitrile solvents such as acetonitrile and propionitrile.

In step-b) the suitable deprotecting agent is selected from tetrabutylammonium fluoride and the like; the suitable solvent is selected from nitrile solvents, ester solvents, ketone solvents, ether solvents and the like. Preferably ether solvents such as tetrahydrofuran, 1,4-dioxane and the like.

In step-c) the suitable coupling agent is selected from HATU, EDC.HCl, HOBt and HOSu. Preferably HATU; the suitable alkylamine is selected from diisopropylethylamine triethyl amine, diethylamine, trimethylamine, methyl amine, ethyl amine, tripropylamine. Preferably diisopropylethylamine; the organic solvent is selected from halo hydrocarbon solvents, nitrile solvents, ester solvents, ketone solvents, ether solvents and the like. Preferably chloro solvents such as dichloromethane and the like.

The ninth aspect of the present invention provides crystalline form of Romidepsin (hereinafter designated as "Form-M") characterized by;
a) its PXRD pattern substantially in accordance with FIG. 1,
b) its powder X-Ray diffractogram having peaks at 8.4, 8.6, 9.1, 9.5, 11.0, 18.2, 21.3 and 23.8±0.2 degrees of two-theta.

Further aspect of the present invention provides a process for the preparation of crystalline form-M of Romidepsin compound of formula-I, comprising the following steps of:
a) subjecting crude Romidepsin of formula (I) to chromatography to form a product, wherein the chromatography is carried out using an achiral stationary phase comprising silica and an eluent comprising acetonitrile and water; and
b) isolating the crystalline form-M of Romidepsin.

PXRD analysis of the present invention was carried out using BRUKER-AXS D8 Advance model X-Ray diffractometer using Cu-Ka radiation of wavelength 1.5406 A° and at continuous scan speed of 0.03°/min.

The best mode of carrying out the present invention is illustrated by the below mentioned examples. These examples are for illustrative purposes only and in no way limit the embodiments of the present invention.

EXAMPLES

Example-1: Preparation of (E)-ethyl 5-(tritylthio) pent-2-enoate of Formula (X)

Triphenylphosphine (100 gm) was added to the mixture of toluene (500 ml) and water (500 ml) at 25-30° C. and stirred it for 5-10 minutes. Ethyl-2-bromo acetate (70 gm) was added to the reaction mixture at 25-30° C. Heated the reaction mixture to 100-105° C. and stirred it for 6 hours at the same temperature. Cooled the reaction mixture to 25-30° C. Both the aqueous layer and organic layer were separated and the aqueous layer was extracted with dichloromethane. Combined the organic layers and basified it with using aqueous sodium hydroxide solution at below 10° C. Organic and aqueous layers were separated and the organic layer was cooled to 0-5° C. 3-(Tritylthio)propanal (101.4 gm) in dichloromethane (300 ml) was added to the above organic layer at 0-5° C. and stirred the reaction mixture for 2 hours at the same temperature. Distilled off the solvent completely from the organic layer under reduced pressure. The obtained compound was recrystallized from methanol to get pure white crystalline title compound.

Yield: 87.6 gms; melting range: 70-72° C.

Example 2: Preparation of (E)-5-(tritylthio)pent-2-en-1-ol of Formula (XI)

The solution of (E)-ethyl 5-(tritylthio)pent-2-enoate (50 gm) in toluene (250 ml) was cooled to 0-5° C. DIBAL-H (44.16 gm) was added to the reaction mixture under nitrogen atmosphere at 0-5° C. and stirred it for 3 hours at the same temperature. The reaction mixture was quenched with ethyl acetate at 0-5° C. Water was added to the above reaction mixture at 0-5° C., further raised the temperature of the reaction mixture to 25-30° C. for 3 hours. Hyflow was added to the reaction mixture, filtered and washed with ethyl acetate (50 ml). The organic layer and aqueous layer both are separated from the filtrate and distilled off the solvent completely from the organic layer under reduced pressure. Toluene was added to the above obtained residue at 25-30°

C. The reaction mixture was cooled to 0-5° C. and stirred it for 1 hour at the same temperature. Filtered the precipitated solid, washed with toluene and dried to get the title compound.

Yield: 38.8 gms; Melting range 105-110° C.

Example 3: Preparation of (E)-5-(tritylthio)pent-2-enal of Formula (VIII)

$MnO_2$ (241.2 gms) was added to the solution of (E)-5-(tritylthio)pent-2-en-1-ol (50 gms) in dichloromethane (1000 ml) at 25-30° C. Heated the reaction mixture to 40-45° C. and stirred it for 4 hours. The reaction mixture was cooled to 25-30° C. and filtered. $MnO_2$ (120.6 gms) was added the filtrate at 25-30° C. Heated the reaction mixture to 40-45° C. and stirred it for 4 hours at the same temperature. The reaction mixture was cooled to 25-30° C. and filtered it. Distilled off the solvent completely from the filtrate under reduced pressure. Isopropanol (150 ml) was added to the obtained compound at 25-30° C. and stirred it for 1 hour. Filtered the solid, washed with isopropanol and dried to get the title compound.

Yield: 40.5 gms; Melting range: 116-120° C.

Example 4: Preparation of (S,E)-3-hydroxy-1-((R)-4-isopropyl-2-thioxothiazolidin-3-yl)-7-(tritylthio) hept-4-en-1-one Cooled the mixture of (R)-1-(4-isopropyl-2-thioxothiazolidin-3-yl)ethanone (9 gms) and dichloromethane (250 ml) to 0-5° C. To this resulting reaction mixture, $TiCl_4$ (9.2 gms) was added at 0-5° C. and stirred for 10-15 minutes. The reaction mixture was cooled to −78° C. Diisopropylethylamine (8.48 ml) was slowly added to the reaction mixture at −78° C. and stirred it for 2 hours at the same temperature. A solution of (E)-5-(Tritylthio)pent-2-enal (9.5 gms) in dichloromethane (250 ml) was slowly added to the reaction mixture at −78° C. and stirred it for about 30 minutes at the same temperature. Quenched the reaction mixture by adding aqueous ammonium chloride solution at 25-30° C. Organic and aqueous layers were separated and the organic layer was washed with water and distilled off solvent completely from the organic layer under reduced pressure to get titled compound.

Yield: 12 gms.

Example 5: Preparation of (S,E)-3-hydroxy-7-(tritylthio)hept-4-enoic acid

Cooled the mixture of (S,E)-3-Hydroxy-1-((R)-4-isopropyl-2-thioxothiazolidin-3-yl)-7-(tritylthio)hept-4-en-1-one (25 gms) and tetrahydrofuran (250 ml) to 0-5° C. To this solution, $LiOH.H_2O$ (9.33 gms) in water (250 ml) was slowly added at 0-5° C. Raised the temperature of the reaction mixture to 25-30° C. and stirred it for 12 hours at the same temperature. Distilled off the solvent from the reaction mixture. To the obtained reaction mixture, methyl tertiary butyl ether was added and both the organic and aqueous layers were separated. Dichloromethane was added to the aqueous layer and acidified with 2N hydrochloric acid at 0-5° C. and stirred it for 30 min at 0-5° C. Organic layer was separated and distilled off the solvent completely from the organic layer to provide the title compound.

Yield: 13 gms.

Example 6: Preparation of (S,E)-2-(trimethylsilyl) ethyl 3-hydroxy-7-(tritylthio)hept-4-enoate Cooled the mixture of (S,E)-3-Hydroxy-7-(tritylthio)hept-4-enoic acid (2 gms) and dichloromethane (20 ml) to 0-5° C. To this reaction mixture, 2-(trimethylsilyl)ethanol (2.15 ml) and dimethylaminopyridine (0.12 gm) were added at 0-5° C. and stirred the reaction mixture for 10 minutes at the same temperature. To this reaction mixture, DCC solution (1.24 gms of DCC dissolved in 10 ml of dichloromethane) was added at 0-5° C. and stirred it for 45 minutes at the same temperature. Raised the temperature of the reaction mixture to 25-30° C., filtered the reaction mixture and washed with dichloromethane. Aqueous sodium bicarbonate solution was added to the obtained filtrate and stirred for 20 minutes. The organic layer was separated, washed with water. Distilled off the solvent completely from the organic layer under reduced pressure to get the title compound.

Yield: 2.5 gms.

Example 7: Preparation of (S,E)-2-(trimethylsilyl) ethyl 3-(((S)-2-((((9H-fluoren-9-yl) methoxy)carbonyl)amino)-3-methyl butanoyl)oxy)-7-(tritylthio) hept-4-enoate Cooled the mixture of the compound obtained in example 6 and dichloromethane (25 ml) to 0-5° C. Fmoc-L-Valine (2.2 gms) and dimethylaminopyridine (0.058 gm) were added to the reaction mixture at 0-5° C. and stirred it for 10 minutes. To this reaction mixture, DCC solution (1.39 gms of DCC dissolved in 5 ml of dichloromethane) was slowly added at 0-5° C. The reaction mixture temperature was raised to 25-30° C. and stirred it for about 6 hours. The reaction mixture was filtered and washed with dichloromethane. Aqueous sodium bicarbonate solution was added to the filtrate and stirred for 20 minutes. Separated both the aqueous and organic layers and the organic layer was washed with water. Distilled off the solvent from the organic layer under reduced pressure to get the title compound.

Yield: 3.4 gms.

Example 8: Preparation of the Compound of Formula (II)

Dissolved 7 gms of (S,E)-2-(trimethylsilyl)ethyl 3-(((S)-2-((((9H-fluoren-9-yl) methoxy) carbonyl) amino)-3-methyl butanoyl)oxy)-7-(tritylthio)hept-4-enoate in 50 mol of acetonitrile at 25-30° C. To this solution, triethylamine (6.20 ml) was added at 25-30° C. and stirred it for 28 hours at the same temperature. Distilled off the solvent completely from the reaction mixture under reduced pressure. To the obtained compound, water (50 ml) and dichloromethane (50 ml) were added and stirred for about 15 minutes. Both the organic layer and aqueous layer were separated and distilled off the solvent completely from the organic layer to get the title compound.

Yield: 2 gms.

Example 9: 3-(Tritylthio) Propionic Acid of Formula (XIX)

To a solution of trityl chloride (100 gm) in toluene (500 ml), 3-mercapto propionic acid (41.9 gms) was added at 25-30° C. and stirred it for 6 hours at 25-30° C. 500 ml of water was added to the reaction mixture at 25-30° C. and stirred it for 15 minutes at the same temperature. Filtered the precipitated solid, washed with water and dried to get title compound.

Yield: 120 gms; Melting Range 200-205° C.

Example 10: 3-(Tritylthio)propan-1-ol of Formula (XX)

A solution of 3-(Tritylthio) propionic acid (100 gms) in tetrahydrofuran (700 ml) was cooled to 0-5° C. To this solution, 13.2 gms of sodium borohydride was added in lot wise at 0-5° C. and stirred it for 10 minutes. To this reaction mixture, BF$_3$-etherate (56.9 ml) was slowly added at 0-5° C. The temperature of the reaction mixture was raised to 25-30° C. and stirred it for 3 hours. Cooled the reaction mixture to 0-5° C. and water (700 ml) followed by dichloromethane (800 ml) were added to the reaction mixture. Raised the temperature of the reaction mixture to 25-30° C. and stirred it for 10 minutes. Both the organic and aqueous layers were separated and the organic layer was washed with aqueous sodium chloride solution. Distilled off the solvent completely from the organic layer under reduced pressure and co-distilled with cyclohexane. Cyclohexane (100 ml) was added to the obtained compound at 25-30° C. and heated the reaction mixture to 55-60° C. The reaction mixture was stirred for 45 minutes at 55-60° C. The reaction mixture was cooled to 25-30° C. and stirred for 30 minutes. Filtered the precipitated solid, washed with cyclohexane and dried to get the title compound.

Yield: 75 gms. M.R.:98-102° C.

Example 11: 3-(Tritylthio)propanal of Formula (IX)

Cooled the mixture of dichloromethane (300 ml) and oxalyl chloride (22.7 ml) to −75 to −70° C. To this reaction mixture, dimethylsulfoxide (38.3 ml) was added slowly at −75 to −70° C. and stirred it for 2 hours at the same temperature. A solution of 3-(tritylthio)propan-1-ol (50 gms) in dichloro methane (350 ml) was slowly added to the above reaction mixture at −75 to −70° C. and stirred it for about 2 hours at the same temperature. To this reaction mixture, triethylamine (125 ml) was slowly added at −75 to −70° C. and stirred the reaction mixture for 2 hours at 0-5° C. Water (350 ml) was added to the reaction mixture at 0-5° C. The temperature was raised to 25-30° C. Both the organic and aqueous layers were separated and the organic layer was washed with aqueous sodium thiosulfate solution. Distilled off the solvent completely from organic layer under reduced pressure and co-distilled with cyclohexane. Cyclohexane (150 ml) was added to the obtained compound at 25-30° C. and stirred it for 40 minutes at the same temperature. Filtered the solid, washed with cyclohexane and dried the material to get the title compound.

Yield: 40.5 gms. M.R.: 103-105° C.

Example 12: Preparation of (S)-2-(((9H-fluoren-9-yl)methoxy)carbonylamino)-3-(tritylthio) Propanoic Acid Trityl chloride (137.8 gms) was added to the solution of (S)-2-Amino-3-mercaptopropanoic acid (50 gms) in dimethylformamide (150 ml) at 25-30° C. Heated the reaction mixture to 40-50° C. and stirred it for 4 hours at same temperature. The reaction mixture was cooled to 25-30° C., and slowly added to the aqueous sodium acetate solution and stirred it for 25 minutes. Filtered the precipitated solid and washed with water. Methyl tertiary butyl ether (1000 ml) was added to the obtained compound at 25-30° C. and stirred it for 10 minutes. Filtered the solid, washed with methyl tertiary butyl ether. The obtained compound was added to the aqueous sodium bicarbonate solution at 25-30° C. Tetrahydrofuran was added to the reaction mixture at 25-30° C. and cooled the reaction mixture to 0-5° C. Fmoc-Cl (53 gms) was added to the reaction mixture at 0-5° C. and stirred it for 1 hour at the same temperature. Aqueous sodium bicarbonate solution followed by Fmoc-Cl (42.7 gms) were slowly added to the reaction mixture at 0-5° C. and stirred it for 1 hour at the same temperature. Acidified the reaction mixture with dilute hydrochloride solution and separated the both organic and aqueous layers. The aqueous layer was extracted with methyl tertiary butyl ether and combined the organic layers and distilled off the solvent completely under reduced pressure. The obtained compound was dissolved in 200 ml of dichloromethane at 25-30° C. Pet.ether (1050 ml) was added to the reaction mixture at 25-30° C. and stirred for 6 hours at the same temperature. Filtered the precipitated solid and dried the material to get the title compound.

Yield: 180 gms.

Example 13: Preparation of (2S,3R)-methyl 2-((S)-2-amino-3-(tritylthio)propanamido)-3-hydroxy Butanoate A mixture of (2S,3R)-methyl-2-amino-3-hydroxy butanoate hydrochloride and dichloromethane (500 ml) was cooled to 0-5° C. To this reaction mixture, N-methyl morpholine (37.42 ml) was added at 0-5° C. and stirred for 30 minutes at the same temperature. (S)-2-(((9H-fluoren-9-yl)methoxy) carbonylamino)-3-(tritylthio)propanoic acid (100 gms), hydroxy benzotriazole (4.61 gms) and DCC solution (42.27 gms of DCC in 100 ml of dichloromethane) were added to the reaction mixture at 0-5° C. and stirred for 30 minutes at the same temperature. Raised the temperature of reaction mixture to 25-30° C. and stirred for 4 hours at the same temperature. Distilled off the reaction mixture was under reduced pressure. To the above obtained compound, acetonitrile (250 ml) and triethylamine (71.68 ml) were added at 25-30° C. and stirred the reaction mixture for 30 mins at the same temperature. The precipitate byproduct was filtered and washed with acetonitrile. Stirred the filtrate was for 12 hours at 25-30° C. Distilled off the solvent from reaction mixture under reduced pressure. Dichloromethane (300 ml) was added to the obtained compound at 25-30° C. and cooled to 0-5° C. and stirred for 30 minutes. The reaction mixture was filtered through hiflow bed and washed with dichloromethane. Water was added to the filtrate at 25-30° C. and stirred for 10 minutes. Separated the both aqueous and organic layers and distilled off the solvent from the organic layer under reduced pressure. To this residue compound, methyl tertiary butyl ether (200 ml) was added at 25-30° C. and stirred for 25 minutes at the same temperature. Cooled the reaction mixture to 0-5° C. and stirred the reaction mixture for 3 hours at the same temperature. Filtered the precipitated solid and washed with methyl tertiary butyl ether. To the obtained compound, dichloromethane (300 ml) was added at 25-30° C. and stirred for 30 minutes. Filtered the reaction mixture through hyflow bed and washed with dichloromethane. Distilled off the solvent completely from filtrate under reduced pressure. Methyl tertiary butyl ether (200 ml) followed by dichloromethane (50 ml) were added to the obtained compound at 25-30° C. Cooled the reaction mixture to 0-5° C. and stirred for 2 hours at the same temperature. Filtered the solid, washed with methyl tertiary butyl ether and dried to get the title compound.

Yield: 60 gms. M.R.: 132-135° C.

Example 14: (5R,8S,11S,12R)-Methyl 1-(9H-fluoren-9-yl)-12-hydroxy-5-isopropyl-3,6,9-trioxo-8-(tritylthiomethyl)-2-oxa-4,7,10-triazatridecane-11-carboxylate (2S,3R)-Methyl 2-((S)-2-amino-3-(tritylthio)propanamido-3-hydroxy butanoate (100 gms) was dissolved in dichloromethane (1300 ml) at 25-30° C. and cooled to 0-5° C. To this reaction mixture, Fmoc D-valine (69.3 gms) was added at 0-5° C. and stirred for 10 minutes, at the same temperature. To the above reaction mixture, N-methyl morpholine (34.4 ml), hydroxybenzotriazole (5.6 gms), dicyclohexylcarbodiimide solution (51.6 gms of DCC dissolved in 200 ml of dichloromethane) were added at 0-5° C. and stirred it for 25-30 minutes at the same temperature. The reaction mixture temperature was raised to 25-30° C. and stirred for 3 hours. The obtained reaction mixture was filtered and washed with dichloromethane. The filtrate was washed with aqueous sodium bicarbonate solution followed by aqueous sodium chloride solution. Distilled off the solvent completely from the organic layer under atmospheric pressure. Ethyl acetate (700 ml) was added to the above obtained compound at 25-30° C. and stirred it for 30 minutes. The reaction mixture was cooled to 0-5° C. and stirred for 2 hours. The obtained compound was filtered, washed with ethyl acetate and dried to get the title compound.

Yield: 151 gms. M.R.: 148-150° C.

Example 15: (5R,8S,11S,12R)-Methyl 1-(9H-fluoren-9-yl)-12-methanesulfonyloxy-5-isopropyl-3,6,9-trioxo-8-(tritylthiomethyl)-2-oxa-4,7,10-triazatridecane-1-carboxylate (6R,9S,12S,13R) Methyl 13-hydroxy-6-isopropyl-2,2-dimethyl-4,7,10-trioxo-9-(tritylthiomethyl)-3-oxa-5,8,11-triazatetradecane-12-carboxylate (160 gms) was dissolved in dichloromethane (1600 ml) at 25-30° C. and cooled it to 0-5° C. To this reaction mixture, dimethylaminopyridine (0.97 gms), triethylamine (42 ml), methanesulfonyl chloride (19.16 ml) were added at 0-5° C. and stirred for 3 hours at the same temperature. The obtained reaction mixture was washed with aqueous ammonium chloride solution followed by aqueous sodium chloride solution. Distilled off the solvent completely from the reaction mixture under reduced pressure and co-distilled with cyclohexane. Cyclohexane (640 ml) was added to the obtained compound at 25-30° C. and stirred for 30 mins at the same temperature. Filtered the solid, washed with cyclohexane and dried to get the title product.

Yield: 153 gms.

Example 16: Preparation of (Z)-methyl 2-((S)-2-((R)-2-amino-3-methylbutanamido)-3-(tritylthio)propanamido)but-2-enoate (5R,8S,11S,12R)-Methyl 1-(9H-fluoren-9-yl)-12-hydroxy-5-isopropyl-3,6,9-trioxo-8-(tritylthiomethyl)-2-oxa-4,7,10-triazatridecane-11-carboxylate (165 gms) was dissolved in dichloromethane (1650 ml) at 25-30° C. and cooled it to 0-5° C. To this reaction mixture, 1,4-diazabicyclo[2.2.2]octane (DABCO) (210 gms) was added at 0-5° C. and stirred it for 3 hours at the same temperature. The reaction temperature was raised to 25-30° C. and stirred it for 8 hours at the same temperature. The reaction mixture was filtered and washed with dichloro methane. The filtrate was washed with water. Distilled off the solvent completely from the organic layer under reduced pressure. Acetonitrile (660 ml) was added to the above distillate and stirred for 2 hours. The reaction mixture was washed with cyclohexane. Distilled off the acetonitrile solvent completely from the reaction mixture under reduced pressure to get the title compound.

Yield: 84 gms.

Example 17: Preparation of the Compound of Formula (III)

The mixture of the title compound of example 16 (50 gms) and tetrahydrofuran (600 ml) was cooled to 0-5° C. To this reaction mixture, aqueous LiOH was added at 0-5° C. and stirred for 6 hours. Acidified the reaction mixture with 1N HCl solution at 0-5° C. The compound was extracted with ethyl acetate. Distilled off the solvent completely from the organic layer under reduced pressure. The obtained compound was co-distilled with methyl tertiary butyl ether (MTBE). MTBE was added to the above distillate and stirred for 45 mins. The obtained compound was filtered and washed with MTBE. The above obtained compound was dissolved in tetrahydrofuran (600 ml) at 25-30° C. Aqueous sodium bicarbonate solution was added to the above reaction mixture and cooled to 0-5° C. To this reaction mixture, Fmoc-Cl was added and stirred for 30 mins. Acidified the reaction mixture with 1N HCl solution. Ethyl acetate was added to the reaction mixture and both aqueous and organic layers were separated. Distilled off the solvent completely from the organic layer under reduced pressure and co-distilled with dichloromethane. Dichloromethane (150 ml) was added to the reaction mixture and heated to 40-45° C. and stirred it for 15-20 minutes at same temperature. Filtered the reaction mixture through highflow bed and washed with dichloromethane. Diisopropyl ether (400 ml) was slowly added to the filtrate at 25-30° C. and stirred for 3 hours at same temperature. The precipitated solid was filtered, washed with diisopropyl ether and dried to get the title compound.

Yield: 22 gms

Example 18: Preparation of the Compound of Formula (IV)

The mixture of the compound of formula II (2 gms), the compound of formula-III (3.3 gms) and dichloromethane (20 ml) was stirred for 5-10 mins at 25-30° C. To this reaction mixture, HATU (1.70 gms), HOBt (0.87 gms) and DIPEA (1.41 ml) were slowly added at 25-30° C. and stirred the reaction mixture for 13 hours at 25-30° C. Water was added to the above reaction mixture at 25-30° C. and stirred for 10 mins at the same temperature. Both the organic and aqueous layers were separated and distilled off the solvent completely from the organic layer under reduced pressure to get the title compound.

Yield: 3 gms.

Example 19: Preparation of the Compound of Formula (V)

Diethylamine (1.9 gms) was added to the mixture of the compound of formula IV (7 gms) and acetonitrile (70 ml) at 25-30° C. Stirred the reaction mixture for 12 hours at 25-30° C. Distilled off the solvent completely from reaction mixture under reduced pressure to get the title compound.

Yield: 4.2 gms

Example 20: Preparation of the Compound of Formula (VI)

Tetrabutyl ammonium fluoride (0.683 gms) was added to the mixture of the compound of formula V (1.5 gms) and tetrahydrofuran (50 ml) at 25-30° C. and stirred the reaction mixture for 18 hrs at the same temperature. Distilled off the solvent completely from the reaction mixture under reduced pressure to get the title compound.

Yield: 1.2 gms

Example 21: Preparation of the Compound of Formula (VII)

HATU (2 gms) and DIPEA (1.4 gms) were added to the mixture of the compound of formula VI (2 gms) and dichloromethane (200 ml) at 25-30° C. Stirred the reaction mixture for 2 days at 25-30° C. Quenched the reaction mixture with aqueous ammonium chloride solution and stirred for 30 mins at 25-30° C. Both the organic and aqueous layers were separated and the organic layer was washed with water. Distilled off the solvent completely from organic layer under reduced pressure to get a title compound.

Yield: 1.37 gms

Example 22: Alternate Process for the Preparation of the Compound of Formula (VII)

A mixture of the compound of formula IV (2 gms) and acetonitrile (70 ml) was cooled to 0-5° C. To this reaction mixture, tetrabutyl ammonium fluoride tri hydrate (3.8 gms) was added at 0-5° C. The temperature of the reaction mixture was raised to 25-30° C. and stirred it for 2 hours at the same temperature. Distilled-off the solvent completely from the reaction mixture under reduced pressure. Dichloromethane (200 ml) was added to the obtained compound at 25-30° C. To this reaction mixture, HATU (2 gms) and diisopropyl ethylamine (1.4 gms) were added at 25-30° C. and stirred for 20 hours at the same temperature. Quenched the reaction mixture with aqueous ammonium chloride solution at 25-30° C. and stirred for 30 mins. Both the organic and aqueous layers were separated and the organic layer was washed with water. Distilled off the solvent completely from organic layer under reduced pressure to get a title compound.

Yield: 0.75 gms

Example 23: Preparation of Romidepsin (Formula I)

The compound of formula VII (2 gms) was dissolved in the mixture of dichloromethane (200 ml) and methanol (200 ml) at 25-30°. This reaction mixture was added to the mixture of iodine (0.1 gms), dichloromethane (1000 ml) and methanol (1000 ml) at 25-30° C. and stirred the reaction mixture for 2 hours at same temperature. The reaction mixture was cooled to 0-5° C. and aqueous sodium thiosulphate solution was added it at 0-5° C. and stirred the reaction mixture for 10 minutes. Both the organic and aqueous layers were separated and the organic layer was washed with water. Distilled off the solvent completely from organic layer under reduced pressure. The obtained compound was purified by column chromatography using dichloromethane and methanol mixture as eluents. The compound was isolated by using n-hexane.

Yield: 0.4 gms.

Example 24: Alternative Process for the Preparation of (5R,8S,14S,Z)-(S,E)-1-oxo-1-(2-(trimethylsilyl) ethoxy)-7-(tritylthio) hept-4-en-3-yl 11-ethylidene-1-(9H-fluoren-9-yl)-5,14-diisopropyl-3,6,9,12-tetraoxo-8-((tritylthio) methyl)-2-oxa-4,7,10,13-tetraazapenta decan-15-oate (Formula IV)

The solution of (S,E)-3-Hydroxy-7-(tritylthio)hept-4-enoic acid (25 gms) and dichloromethane (175 ml) was cooled to −20 to −15° C. To this reaction mixture, 2-(trimethylsilyl)ethanol (10.5 gm) and dimethylaminopyridine (0.73 gm) were added at −20° C. to −15° C. and stirred for 10 minutes at same temperature. To this reaction mixture, dicyclohexyl carbodiimide solution (18.4 gms of DCC dissolved in 125 ml of dichloromethane) was added at −20° C. to −15° C. and raised the temperature to 0-5° C. and stirred the reaction mixture for 3 hrs. Quenched the reaction by adding aqueous ammonium chloride solution and raised the reaction mixture temperature to 25-30° C. Filtered the reaction mixture and washed with dichloromethane. Separated the organic and aqueous layers from the filtrate. Washed the organic layer with aqueous sodium bicarbonate solution. The organic layer was dried with sodium sulfate and cooled the organic layer to 0-5° C. Fmoc-L-Valine (30 gms) and dimethylaminopyridine (0.73 gm) were added to the reaction mixture at 0-5° C. and stirred for 15 min. To this reaction mixture, DCC solution (18.8 gms of DCC dissolved in 125 ml of dichloromethane) was slowly added at 0-5° C. The reaction mixture temperature was raised to 25-30° C. and stirred for about 6 hours at same temperature. Quenched the reaction mixture by adding aqueous ammonium chloride solution at 25-30° C. Filtered the reaction mixture and washed with dichloromethane. Separated both the organic and aqueous layers. Washed the organic layer with aqueous sodium bicarbonate solution. Distilled off the solvent completely from the organic layer under reduced pressure. Acetonitrile (125 ml) was added to the above obtained compound at 25-30° C. To this reaction mixture, diethylamine (61.53 ml) was added at 25-30° C. and stirred for 4 hours at the same temperature. Aqueous ammonium chloride solution followed by toluene were added to the reaction mixture at 25-30° C. and stirred for 45 min at the same temperature. Separated both the organic and aqueous layers. Cooled the organic layer to 10-15° C. and washed with aqueous acetic acid solution twice. The organic layer was washed with the aqueous sodium bicarbonate solution. The organic layer was cooled to 0-5° C. To the reaction mixture, (5R,8S,Z)-11-ethylidene-1-(9H-fluoren-9-yl)-5-isopropyl-3,6,9-trioxo-8-((tritylthio)methyl)-2-oxa-4,7,10-triazadodecan-12-oic acid (22.93 gms) and HOBt (8.0 gms) were added at 0-5° C. DIPEA (12.46 ml) was added to the pre-cooled mixture of acetonitrile (250 ml) and EDC. HCl (11.46 gms) and this mixture was slowly added to the above reaction mixture at 0-5° C. and stirred it for 5 hrs at same temperature. Quenched the reaction by adding aqueous ammonium chloride solution at 0-5° C. and raised the temperature of the reaction mixture to 25-30° C. Separated both the organic and aqueous layers. The organic layer was washed with aqueous sodium bicarbonate solution. Distilled off the solvent completely from the organic layer under reduced pressure. Purified the obtained compound by column chromatography using the mixture of cyclohexane and ethyl acetate as eluents. The obtained pure compound was isolated by using n-heptane to get the pure title compound. Yield: 14 gms. M.R.: 88.5-95.1° C. Chiral purity by HPLC: 99.49%, RSZRR isomer: 0.11% & mixture of RSZSR and RSZRS: 0.4%.

Example 25: Alternative Process for the Preparation of (3S,9S,12R,16S,Z)-6-ethylidene-3,12-diisopropyl-16-((E)-4-(tritylthio)but-1-en-1-yl)-9-((tritylthio) methyl)-1-oxa-4,7,10,13-tetraazacyclohexa-decane-2,5,8,11,14-pentaone (The Compound of Formula VII)

Diethylamine (19 ml) was added to the mixture of (5R, 8S,14S,Z)-(S,E)-1-oxo-1-(2-(trimethylsilyl)ethoxy)-7-(tritylthio) hept-4-en-3-yl 11-ethylidene-1-(9H-fluoren-9-yl)-5,14-diisopropyl-3,6,9,12-tetraoxo-8-((tritylthio) methyl)-2-oxa-4,7,10,13-tetraazapenta decan-15-oate (the compound of formula IV) (50 gms) and acetonitrile (300 ml and stirred it for 3 hours. The reaction was quenched by adding aqueous ammonium chloride solution at 25-30° Dichloromethane was added to the reaction mixture at 25-30° C. Separated both the organic and aqueous layers and the aqueous layer was extracted with dichloromethane. Distilled off the solvent completely from the organic layer. Tetrahydrofuran (500 ml) was added to the above obtained compound at 25-30° C. under nitrogen atmosphere. Tetrabutyl ammonium fluoride (47.7 gms) was added to the reaction mixture at 25-30° C. and stirred the reaction mixture for 6 hrs at the same temperature. The reaction was quenched with aqueous ammonium chloride solution at 25-30° C. Dichloromethane (500 ml) was added to the reaction mixture at 25-30° C. Separated both the organic layer and aqueous layers and the organic layer was dried with sodium sulfate. Cooled the mixture of dichloromethane (3750 ml), HATU (13.8 gms) and NMM (4.9 gms) to 0-5° C. and stirred it for 15 hours at the same temperature. Slowly added the above dried organic layer into the reaction mixture at 0-5° C.° C. and stirred it for 16 hours at same temperature. Quenched the reaction mixture with aqueous ammonium chloride solution at 0-5° C. Raised the temperature of the reaction mixture to 25-30° C. and dichloromethane was added to it. Both the organic and aqueous layers were separated. Distilled off the solvent completely from the organic layer under reduced pressure. The obtained compound was purified by column chromatography using ethyl acetate and cyclohexane as eluents. The obtained compound was further purified by flash chromatography and followed by isolated the title compound as solid. Yield: 25 gms.

Example 26: Process for the Preparation of (1S,4S,7Z,10S,16E,21R)-7-ethylidene-4,21-diisopropyl-2-oxa-12,13-dithia-5,8,20,23-tetraazabicyclo[8.7.6]tricos-16-ene-3,6,9,19,22-pentaone (Romidepsin of Formula I)

Iodine (24.7 gms) was added the mixture of dichloromethane (1800 ml) and methanol (200 ml) at 25-30° C. Cooled the reaction mixture to 0-5° C. To this reaction mixture, a solution of the compound of formula VII (10 gms) in dichloromethane (540 ml) and methanol (60 ml) was slowly added at 0-5° C. Raised the temperature of the reaction mixture to 25-30° C. and stirred it for 60 min at same temperature. Cooled the reaction mixture to 0-5° C. and the reaction mixture was quenched with the aqueous sodium thiosulfate solution. Both the organic and the aqueous layers were separated and the aqueous layer was extracted with dichloromethane. Combined the organic layers and washed with aqueous sodium chloride solution. Distilled off the solvent completely from the organic layer under reduced pressure to get the title compound (Yield: 5.2 gms).

Example-27: Process for the Preparation of Crystalline Form-M of Romidepsin of Formula I 5.0 gms of crude Romidepsin (as obtained in example-26) was dissolved in 100 mL of acetonitrile/water 1/1. The crude product was purified on a preparative HPLC system using silica as stationary phase and acetonitrile/water as eluent. Pure crystalline Form-M of Romidepsin obtained after evaporation of the solvent.

The crystalline Form-M of Romidepsin characterized by:

1. its PXRD pattern substantially in accordance with FIG. 1, 2. its powder X-Ray diffractogram having peaks at 8.4, 8.6, 9.1, 9.5, 11.0, 18.2, 21.3 and 23.8±0.2 degrees of two-theta.

Figure 2:
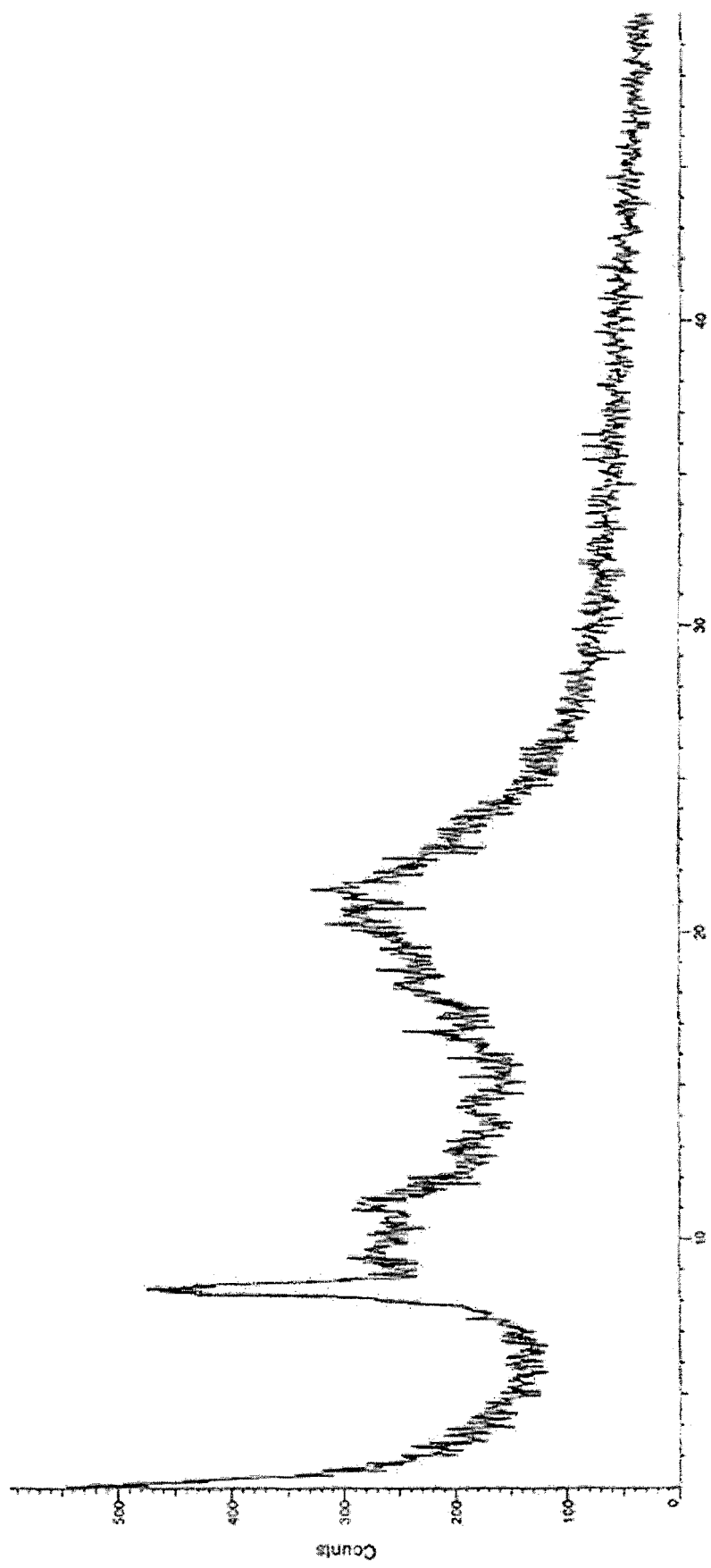

The crystalline Form-M of Romidepsin was lyophilized to get Romidepsin having PXRD diffractogram as depicted in FIG. 2 with peaks at 8.3, 11.1, 21.3±0.2° C. of 2-theta.

We claim:

1. A process for preparation of Romidepsin of formula (I),

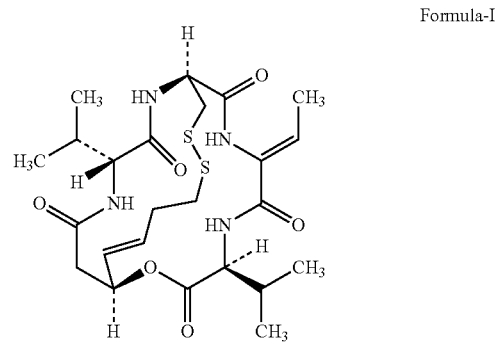 [SMILES: C/C=C1\NC(=O)[C@H]2CSSCC/C=C/[C@H](CC(=O)N[C@H](C(C)C)C(=O)N2)OC(=O)[C@H](C(C)C)NC1=O]

Formula-I comprising:

a) reacting the compound of formula (II) with the compound of formula (III) in presence of a condensing agent and an organic base in an organic solvent to provide compound of formula (IV),

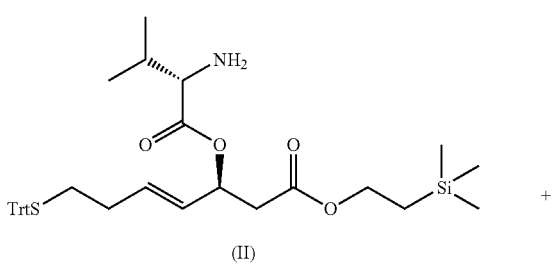

(II)

+

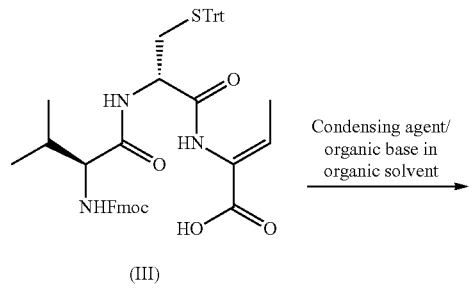

(III)

Condensing agent/ organic base in organic solvent
→

-continued

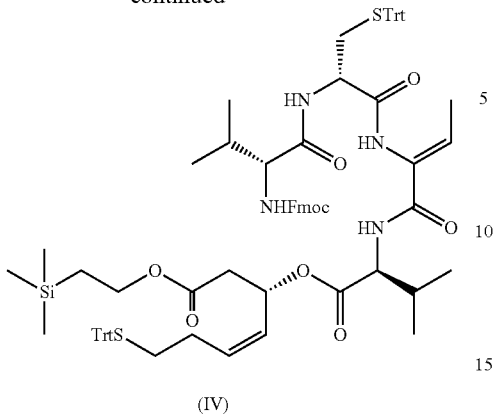

(IV)

wherein, the condensing agent is selected from the group consisting of 1-ethyl-3-(3-dimethylaminopropyl) carbodiimide hydrochloride (EDC.HCl), (1-[bis (dimethylamino) methylene]-1H-1,2,3-triazolo[4,5-b]pyridinium3-oxidhexafluoro phosphate (HATU), hydroxy benzotriazole (HOBt), 1-hydroxy-2,5-pyrrolidinedione (HOSu), dicyclohexylcarbodiimide; and ditolylcarbodiimide optionally in combination with hydroxybenzotriazole or N-hydroxysuccinimide (NHS) or N-hydroxysulfosuccinimide (Sulfo-NHS) or a mixtures thereof, b) reacting the compound of formula (IV) with tetrabutylammonium fluoride in organic solvent to provide compound of formula (VI), and

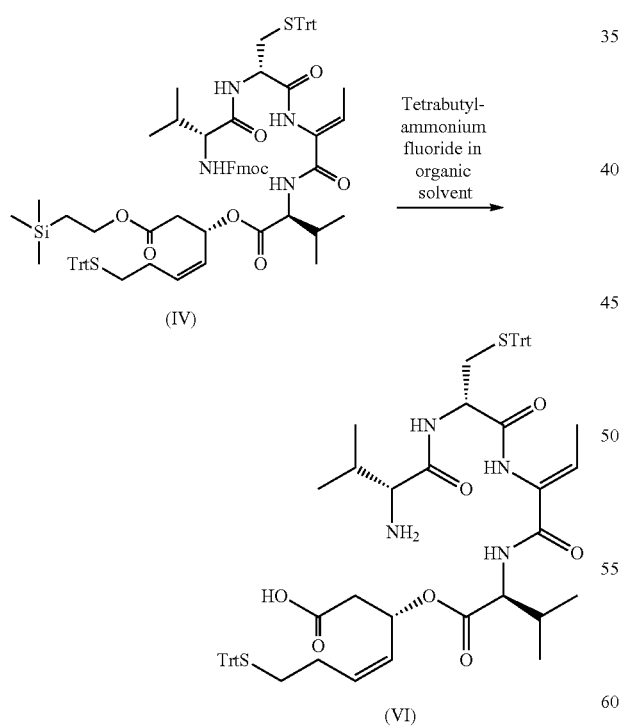

c) converting the compound of formula (VI) to Romidepsin of formula (I).

2. The process of claim 1, wherein the organic base in step-a) is selected from the group consisting of ethylamine, diethylamine, triethylamine, diisopropylethylamine, tripropylamine, triisopropylamine, n-butylamine and a mixture thereof; and wherein the organic solvent in step-a) and step-b) is selected from the group consisting of nitrile solvents, ether solvents, chloro solvents, hydrocarbon solvents, dimethylformamide, dimethylsulfoxide, dimethylacetamide, tetrahydrofuran and N-methylpyrrolidinone.

3. The process of claim 1, wherein (E)-2-(trimethylsilyl)ethyl3-(((S)-2-amino-3-methylbutanoyl)oxy)-7-(tritylthio)hept-4-enoate of formula (II) is prepared by a process comprising:

a) reacting (E)-5-(tritylthio)pent-2-enal of formula (VIII) with (R)-1-(4-isopropyl-2-thioxothiazolidin-3-yl) ethanone in presence of titanium tetrachloride (TiCl$_4$) and diisopropylethylamine (DIPEA), b) washing the product obtained in step-a) with tartaric acid to provide (S,E)-3-hydroxy-1-((R)-4-isopropyl-2-thioxothiazolidin-3-yl)-7-(tritylthio)hept-4-en-1-one free from titanium, c) hydrolyzing the product obtained in step-b) to provide (S,E)-3-hydroxy-7-(tritylthio)hept-4-enoic acid, d) reacting the product obtained in step-c) with 2-(trimethylsilyl)ethanol to provide (S,E)-2-(trimethylsilyl) ethyl 3-hydroxy-7-(tritylthio)hept-4-enoate, and e) reacting the product obtained in step-d) with Fmoc-D-valine to get (S,E)-2-(trimethylsilyl)ethyl 3-(((S)-2-((((9H-fluoren-9-yl) methoxy)carbonyl) amino)-3-methyl butanoyl)oxy)-7-(tritylthio)hept-4-enoate followed by deprotection using triethylamine in acetonitrile to provide compound of formula (II).

4. The process of claim 1, wherein (5R,8S,Z)-1-(9H-fluoren-9-yl)-5-isopropyl-3,6,9-trioxo-8-(tritylthiomethyl)-2-oxa-4,7,10-triazatridec-11-ene-11-carboxylic acid of formula (III) is prepared by a process comprising:

a) reacting the (6R,9S,12S,13R) methyl 13-hydroxy-6-isopropyl-2,2-dimethyl-4,7,10-trioxo-9-(tritylthiomethyl)-3-oxa-5,8,11-triazatetradecane-12-carboxylate of formula (XII) with methanesulfonyl chloride in presence of dimethylaminopyridine (DMAP) in dichloromethane to provide (2S,3R)-methyl 2-amino-3-hydroxybutanoate (5R,8S,Z) methyl 1-(9H-fluoren-9-yl)-5-isopropyl-3,6,9-trioxo-8-(tritylthiomethyl)-2-oxa-4,7,10-triazatridec-11-ene-11-carboxylate, b) reacting the product obtained in step-a) with 1,4-diazabicyclo[2.2.2]octane in dichloromethane to provide (Z)-methyl 2-((S)-2-((R)-2-amino-3-methyl butanamido)-3-(tritylthio)propanamido)but-2-enoate, c) hydrolyzing the product obtained in step-b) using base in a solvent, d) optionally isolating the product obtained in step-c), and e) reacting the product obtained in step-c) or step-d) with Fmoc-Cl to provide compound of formula (III).

5. The process of claim 1, wherein Romidepsin of formula (I) is prepared by a process comprising:

a) reacting the compound of formula (IV) with tetrabutylammonium fluoride in an organic solvent to provide compound of formula (VI), and

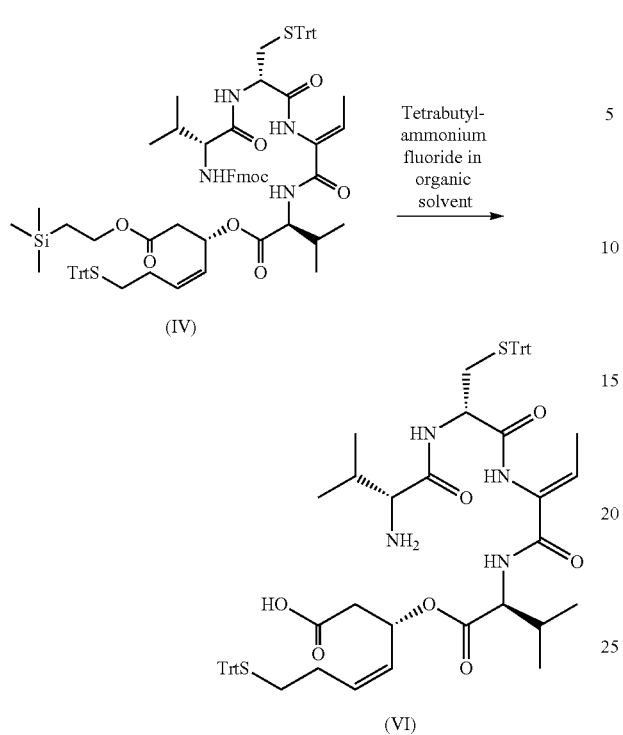

b) converting the compound of formula (VI) to Romidepsin of formula (I).

6. The process of claim 5, wherein the organic solvent in step-a) is selected from the group consisting of nitrile solvents, ether solvents, chloro solvents, hydrocarbon solvents, dimethylformamide, dimethylsulfoxide, dimethylacetamide, tetrahydrofuran and N-methylpyrrolidinone.

7. The process of claim 3, wherein (E)-5-(tritylthio)pent-2-enal of formula (VIII) is prepared by a process comprising:
   a) purifying the (E)-ethyl 5-(tritylthio)pent-2-enoate from a solvent,
   b) reducing the compound obtained in step-a) with a reducing agent in a solvent,
   c) optionally purifying the compound obtained in step-b) using solvent to provide the pure (E)-5-(tritylthio)pent-2-ene-1-ol of formula (XI),
   d) oxidizing the product obtained in step-c) using manganese dioxide (MnO$_2$) in a organic solvent to provide (E)-5-(tritylthio)pent-2-enal, and
   e) optionally purifying the compound obtained in step-d) to provide pure (E)-5-(tritylthio)pent-2-enal of formula (VIII).

8. The process of claim 7, wherein the purification in step-a) is carried out by crystallization, recrystallization or distillation from polar protic solvents, polar aprotic solvents and nonpolar solvents or mixtures thereof.

9. The process of claim 7, wherein (E)-5-(tritylthio)pent-2-enal compound of formula (VIII) free of impurities selected from triphenylphosphine oxide (TPPO), compounds of formulae (Xa) and (Xb) is prepared by a process comprising:
   a) reacting the 3-(tritylthio)propanal of formula (IX) with ethyl 2-(triphenyl phosphoranylidene) acetate in dichloromethane,
   b) purifying the compound obtained in step-a) using methanol to provide pure (E)-ethyl 5-(tritylthio)pent-2-enoate of formula (X),
   c) reducing the compound obtained in step-b) with diisobutyl aluminum hydride (DIBAL-H) in toluene,
   d) purifying the compound obtained in step-c) using toluene to provide pure (E)-5-(tritylthio)pent-2-ene-1-ol of formula (XI),
   e) oxidizing the product obtained in step-d) using manganese dioxide (MnO$_2$) in dichloroethane to provide compound of formula-(VIII), and
   f) purifying the compound obtained in step-e) using isopropanol to provide pure (E)-5-(tritylthio)pent-2-enal of formula (VIII).

10. The process of claim 4, wherein (6R,9S,12S,13R) methyl 13-hydroxy-6-isopropyl-2,2-dimethyl-4,7,10-trioxo-9-(tritylthiomethyl)-3-oxa-5,8,11-triazatetradecane-12-carboxylate of formula (XII) is prepared by a process comprising:
   a) reacting fluorenylmethoxycarbonylamino (D)-tritylthio cysteine of formula (XIV) with (2S,3R) methyl 2-amino-3-hydroxy butanoate hydrochloride of formula (XV) in presence of condensing agent and N-methylmorpholine to produce methyl 2-((S)-2-(((9H)-fluoren-9-yl)methoxycarbonylamino)-3-(tritylthio)propanamido)-3-hydroxy butanoate of formula (XVI),
   b) treating the compound of formula (XVI) with organic base in an organic solvent to provide (2S,3R)-methyl 2-((S)-2-amino-3-(tritylthio)propanamido)-3-hydroxy butanoate of formula (XVII), and
   c) reacting the compound of formula (XVII) with fluorenylmethoxycarbonylamino-D-valine of formula (XVIII) in presence of condensing agent in an organic solvent to provide (6R,9S,12 S,13R) methyl 13-hydroxy-6-isopropyl-2,2-dimethyl-4,7,10-trioxo-9-(tritylthiomethyl)-3-oxa-5,8,11-triazatetradecane-12-carboxylate of formula (XII)
   wherein the condensing agent in step-a) and step-c) is selected from the group consisting of N,N-dicyclohexylcarbodiimide (DCC), hydroxybenzotriazole (HOBt), N-hydroxysuccinimide (HOSu), 3-hydroxy-1,2,3-benzotriazin-4-[3H]-one; an organic base is alkylamine selected from triethylamine, diethylamine, diisopropylethylamine, n-butylamine, and pyridine.

11. The process of claim 10, wherein the organic solvent in step-b) and step-c) is selected from the group consisting of dimethylformamide, dimethylacetamide, dimethylsulfoxide, hydrocarbon solvents, ether solvents, ester solvents, polar aprotic solvents, chloro solvents, ketone solvents, nitrile solvents, alcohol solvents, polar solvents, and a mixtures thereof.

12. The process of claim 9, wherein (E)-5-(tritylthio)pent-2-enal compound of formula (VIII) is prepared by a process comprising:
   a) reacting the 3-(tritylthio)propanal of formula (IX) with ethyl 2-(triphenyl phosphoranylidene)acetate in dichloromethane and then recrystallizing the obtained compound from methanol to provide pure (E)-ethyl 5-(tritylthio)pent-2-enoate of formula (X),
   b) reducing the compound obtained in step-a) using diisobutyl aluminum hydride in toluene and then recrystallizing the obtained compound from toluene to provide the pure (E)-5-(tritylthio)pent-2-ene-1-ol of formula (XI), and c) oxidizing the compound obtained in step-b) using manganese dioxide in dichloromethane and then recrystallizing the obtained compound from isopropanol to provide pure (E)-5-(tritylthio)pent-2-enal of formula (VIII).

13. The process of claim 3, wherein (S,E)-3-hydroxy-7-(tritylthio)hept-4-enoic acid is prepared by a process

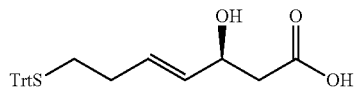

comprising:
a) reacting ((R)-1-(4-isopropyl-2-thioxothiazolidin-3-yl) ethanone with (E)-5-(tritylthio) pent-2-enal in presence of titanium tetrachloride and a base in a organic solvent,
b) washing the product obtained in step-a) with carboxylic acid to provide (S,E)-3-hydroxy-1-((R)-isopropyl-2-thioxothiazolidin-3-yl)-7-(tritylthio)hept-4-en-1-one free from titanium, and
c) converting the product obtained in step-b) to (S,E)-3-hydroxy-7-(tritylthio)hept-4-enoic acid.

14. The process of claim 13,
wherein the base in step-a) is selected from the group consisting of methylamine, dimethylamine, ethylamine, diethylamine, triethylamine, diisopropylethylamine and pyridine; the organic solvent is selected from the group consisting of halohydrocarbon solvents, ether solvents, ester solvents and nitrile solvents; and
wherein the carboxylic acid in step-b) is selected from tartaric acid, citric acid, fumaric acid, malic acid and an aqueous mixtures thereof.

* * * * *